(12) United States Patent
Chin et al.

(10) Patent No.: US 10,492,778 B2
(45) Date of Patent: Dec. 3, 2019

(54) MEDICAL FASTENING DEVICE

(71) Applicant: Surgimatix, Inc., Elk Grove Village, IL (US)

(72) Inventors: Wai N. Chin, Glenview, IL (US); Gary M. Kobylewski, Hoffman Estates, IL (US); Jafar S. Hasan, Oak Brook, IL (US)

(73) Assignee: Surgimatix, Inc., Hillside, IL (US)

( * ) Notice: Subject to any disclaimer, the term of this patent is extended or adjusted under 35 U.S.C. 154(b) by 156 days.

(21) Appl. No.: 15/259,987

(22) Filed: Sep. 8, 2016

(65) Prior Publication Data

US 2016/0374663 A1    Dec. 29, 2016

Related U.S. Application Data

(62) Division of application No. 14/180,884, filed on Feb. 14, 2014, now Pat. No. 9,439,646.
(Continued)

(51) Int. Cl.
    *A61B 17/04* (2006.01)
    *A61B 17/06* (2006.01)
    (Continued)

(52) U.S. Cl.
    CPC ...... *A61B 17/0469* (2013.01); *A61B 17/0401* (2013.01); *A61B 17/0482* (2013.01);
    (Continued)

(58) Field of Classification Search
    CPC ........... A61F 2/0063; A61F 2002/0072; A61B 17/0469; A61B 17/0482; A61B 17/06004;
    (Continued)

(56) References Cited

U.S. PATENT DOCUMENTS

| 4,950,283 A | * | 8/1990 | Dzubow | A61B 17/0466 600/209 |
| 5,074,874 A | * | 12/1991 | Yoon | A61B 17/0469 606/139 |

(Continued)

FOREIGN PATENT DOCUMENTS

| JP | 2016/506858 A | 3/2016 |
| WO | WO 94/05213 A1 | 3/1994 |
| WO | WO 2012/088232 A2 | 7/2012 |

OTHER PUBLICATIONS

International Search Report from corresponding International Patent Application No. PCT/US2014/016442 Report dated Jun. 12, 2014.

*Primary Examiner* — Julian W Woo

(74) *Attorney, Agent, or Firm* — Miller, Matthias & Hull LLP

(57) ABSTRACT

A medical fastening device is provided. The fastening device may include a first arcuate needle adapted to rotate about a first axis in a first direction, entering through a first section of one of a tissue and a prosthetic material, and exiting through a second section of one of the tissue and the prosthetic material; a second arcuate needle adapted to rotate about a second axis in a second direction, entering through the second section of one of the tissue and the prosthetic material, and exiting through the first section of one of the tissue and the prosthetic material; and a drive mechanism operatively coupled to each of the first and second arcuate needles and configured to engage each of the first and second arcuate needles between a retracted position and an extended position.

7 Claims, 24 Drawing Sheets

Related U.S. Application Data

(60) Provisional application No. 61/765,460, filed on Feb. 15, 2013.

(51) Int. Cl.
*A61F 2/00* (2006.01)
*A61B 17/00* (2006.01)

(52) U.S. Cl.
CPC .. *A61B 17/06004* (2013.01); *A61B 17/06166* (2013.01); *A61F 2/0063* (2013.01); *A61B 2017/00398* (2013.01); *A61B 2017/0404* (2013.01); *A61B 2017/0409* (2013.01); *A61B 2017/0417* (2013.01); *A61B 2017/0419* (2013.01); *A61B 2017/0427* (2013.01); *A61B 2017/0472* (2013.01); *A61B 2017/06042* (2013.01); *A61F 2002/0072* (2013.01)

(58) Field of Classification Search
CPC .......... A61B 17/06166; A61B 17/0401; A61B 2017/06042; A61B 2017/00398; A61B 2017/0409; A61B 2017/0417; A61B 2017/0419; A61B 2017/0404; A61B 2017/0427; A61B 2017/0472
See application file for complete search history.

(56) References Cited

U.S. PATENT DOCUMENTS

| | | | |
|---|---|---|---|
| 5,364,408 A | 11/1994 | Gordon | |
| 5,470,338 A | 11/1995 | Whitfield et al. | |
| 5,527,321 A | 7/1996 | Hinchliffe | |
| 5,755,728 A * | 5/1998 | Maki | A61B 17/0469 606/139 |
| 5,855,586 A * | 1/1999 | Habara | A61B 17/12009 606/139 |
| 6,152,935 A * | 11/2000 | Kammerer | A61B 17/0469 606/144 |
| 6,319,263 B1 * | 11/2001 | Levinson | A61B 17/0057 606/144 |
| 6,517,578 B2 * | 2/2003 | Hein | A61F 2/0811 606/232 |
| 6,955,643 B2 | 10/2005 | Gellman et al. | |
| 8,518,078 B2 * | 8/2013 | Sulamanidze | A61B 17/06066 606/144 |
| 8,932,327 B2 * | 1/2015 | Kosa | A61B 17/0401 606/228 |
| 8,932,328 B2 * | 1/2015 | Megaro | A61B 17/06109 606/228 |
| 9,060,768 B2 * | 6/2015 | Ferragamo | A61B 17/0401 |
| 9,237,887 B2 * | 1/2016 | Wack | A61B 17/0483 |
| 9,439,646 B2 | 11/2016 | Chin et al. | |
| 9,675,341 B2 * | 6/2017 | D'Agostino | A61B 17/06133 |
| 2003/0233104 A1 | 12/2003 | Gellman et al. | |
| 2003/0236550 A1 | 12/2003 | Peterson et al. | |
| 2008/0132919 A1 | 6/2008 | Chui et al. | |
| 2009/0093824 A1 | 4/2009 | Hasan et al. | |
| 2010/0152751 A1 | 6/2010 | Meade et al. | |
| 2011/0015654 A1 | 1/2011 | Tsuang | |
| 2012/0165838 A1 | 6/2012 | Kobylewski et al. | |
| 2014/0236193 A1 | 8/2014 | Chin et al. | |

* cited by examiner

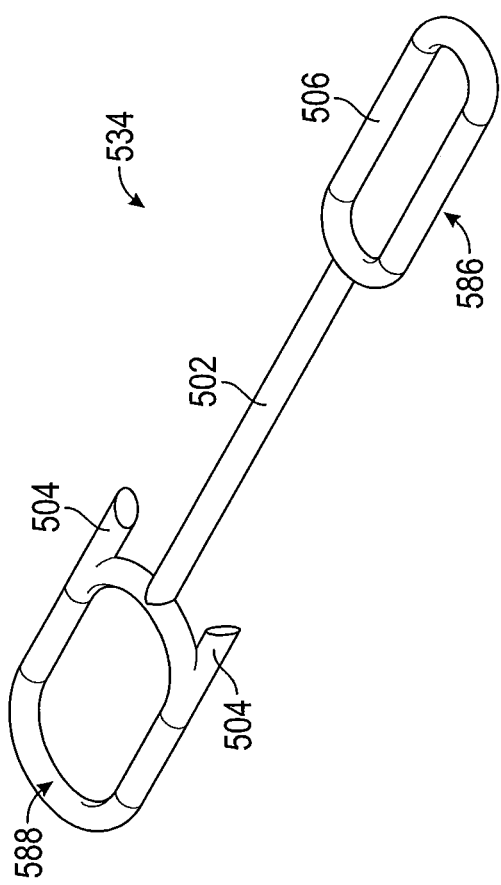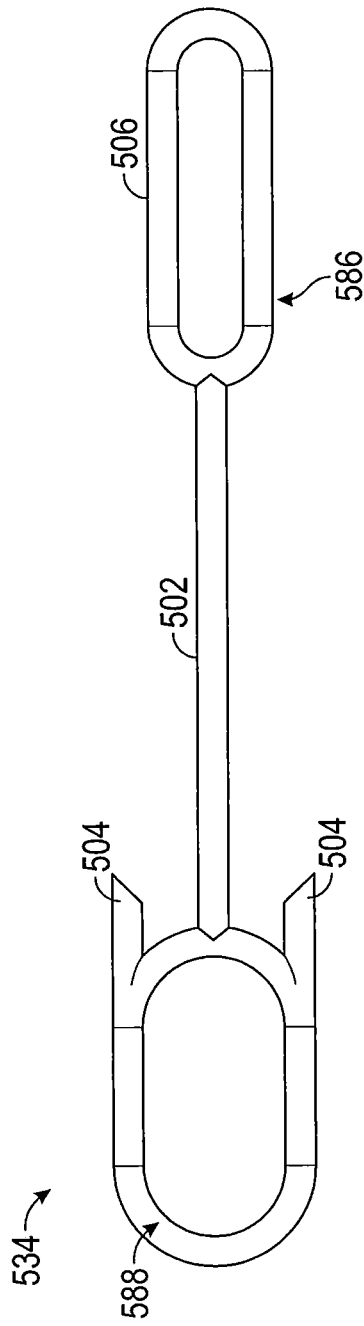

MEDICAL FASTENING DEVICE

CROSS-REFERENCE TO RELATED APPLICATION

This application is a divisional under 35 U.S.C § 121 of U.S. non-provisional patent application Ser. No. 14/180,884, filed on Feb. 14, 2014, which in turn claims the 35 U.S.C. § 119(e) benefit of U.S. Provisional Application Serial No. 61/765,460, filed on Feb. 15, 2013.

FIELD OF THE DISCLOSURE

The present disclosure generally relates to medical devices, and more particularly relates to medical fastening devices for fastening tissue or prosthetic material.

BACKGROUND OF THE DISCLOSURE

The fastening of tissues has long been a need in the medical industry, and correspondingly, a finite number of fastening devices have been developed for different applications and uses. Among these devices are laparoscopic fastening devices or tackers which are often used with minimally invasive procedures such as laparoscopic repair of hernias, and the like. A typical laparoscopic procedure involves the insertion of thin, elongated instruments into relatively small incisions or access ports in the abdomen to access hernia defects in the abdominal wall from the inside. Moreover, the laparoscopic instruments are used to position a prosthetic mesh over the defect and fasten the prosthetic mesh against the inner abdominal wall using tacks, or the like.

Conventional laparoscopic tackers provide a relatively thin and elongated tubular member containing deployable tacks and having an end-firing mechanism positioned at the distal tip thereof. In particular, the end-firing mechanism is configured to deploy tacks directly from the tip of the elongated member in an axial manner, and thus, ideal application suggests positioning the elongated member perpendicularly against the tissue surface to be tacked. However, due to the relatively rigid and elongated nature of the laparoscopic tacker, the limited locations and number of access ports available, and the typical location of hernia defects, it is difficult or near impossible to position the end of the laparoscopic device squarely against the inner wall of the abdomen. In practice, a surgeon using a laparoscopic tacker typically positions the tacker with one hand, sometimes even slightly bending the instrument, while using his other hand to press against the outer wall of the abdomen in order to achieve the best possible angle for installing the tacks.

Furthermore, due to the limited access to hernia defects and the minimally invasive nature of typical hernia repairs, laparoscopic tackers tend to use simple-action type mechanisms to deploy tacks, and correspondingly, employ tacks with simple means for fastening prosthetic mesh to the inner abdominal wall. More specifically, conventional tackers employ screw-type or simple push-type actions to install tacks with threads or barbs which help embed the tacks within abdominal tissue. Over time, in the case of metal, coil-like tacks, these tacks may cause irritation or pain to the patient, become dislodged from the abdominal wall, or cause other complications post surgery. To address such drawbacks associated with metal tacks, absorbable tacks have been developed and employed. Absorbable tacks are designed to be eventually absorbed by the body, and thus, cause less irritation or pain to the patient over time. However, absorbable tacks also tend to provide holding or tensile strength that is less than optimal. In such cases, suturing the hernia defects or suturing prosthetic mesh to the abdominal wall may prove to be more effective. However, the relatively complex nature involved with suturing makes it difficult to use sutures on hernia defects via laparoscopic or otherwise minimally invasive procedures.

Accordingly, there is a need for minimally invasive or laparoscopic means of tissue fastening or installing sutures in tissue which substantially facilitates the installation process for the surgeon or user. There is also a need for a medical fastening device which provides a more effective and reliable means for closing tissue and/or fastening prosthetic mesh to tissue. Furthermore, there is a need for a medical fastening device which employs fasteners that reduce irritation, pain, and other complications to the patient without adversely affecting tissue holding strength.

SUMMARY OF THE DISCLOSURE

In accordance with one aspect of the disclosure, a fastening device is provided. The fastening device may include a first arcuate needle adapted to rotate about a first axis in a first direction, entering through a first section of one of a tissue and a prosthetic material, and exiting through a second section of one of the tissue and the prosthetic material; a second arcuate needle adapted to rotate about a second axis in a second direction, entering through the second section of one of the tissue and the prosthetic material, and exiting through the first section of one of the tissue and the prosthetic material; and a drive mechanism operatively coupled to each of the first and second arcuate needles and configured to engage each of the first and second arcuate needles between a retracted position and an extended position.

In accordance with another aspect of the disclosure, a tissue fastening device is provided. The tissue fastening device may include an elongate member extending between a working end and a control end, the working end having a firing aperture; a first arcuate needle disposed within the firing aperture of the working end and adapted to rotate about a first axis in a first direction, entering through a first section of one of a tissue and a prosthetic material, and exiting through a second section of one of the tissue and the prosthetic material; a second arcuate needle disposed within the firing aperture of the working end and adapted to rotate about a second axis in a second direction, entering through the second section of one of the tissue and the prosthetic material, and exiting through the first section of one of the tissue and the prosthetic material; and a drive mechanism operatively coupled to each of the first and second arcuate needles and configured to engage each of the first and second arcuate needles between a retracted position and an extended position in response to user input received through the control end.

In accordance with another aspect of the disclosure, a tissue fastening device is provided. The tissue fastening device may include an elongate member extending between a working end and a control end, the working end having a firing aperture; an arcuate needle disposed within the firing aperture of the working end and rotatable between a retracted position and an extended position, the arcuate needle including a recess configured to engagably receive an end of a fastener therein; and a drive mechanism operatively coupled to the arcuate needle and configured to, upon actuation, advance the arcuate needle in a forward rotation through one of a tissue and a prosthetic material and engage an end of a fastener to be installed, and upon release, retract the arcuate needle in a reverse rotation through one of the tissue and the prosthetic material to pull the engaged end of the fastener therethrough.

In accordance with yet another aspect of the disclosure, a tissue fastener is provided. The tissue fastener may include an elongated filament having a leading end and a trailing end; a needle guide disposed on the leading end; and a retention member disposed on the trailing end, the retention member being configured to resist advancement through at least one of a tissue and a prosthetic material.

These and other aspects and features of the disclosure will be better understood upon reading the following detailed description when taken into conjunction with the accompanying drawings.

BRIEF DESCRIPTION OF THE DRAWINGS

FIG. 41 is a perspective view of another fastener having an interlocking configuration adapted for use with a single-needle fastening device;

FIG. 42 is a top plan view of the fastener of FIG. 41;

Figure 1:
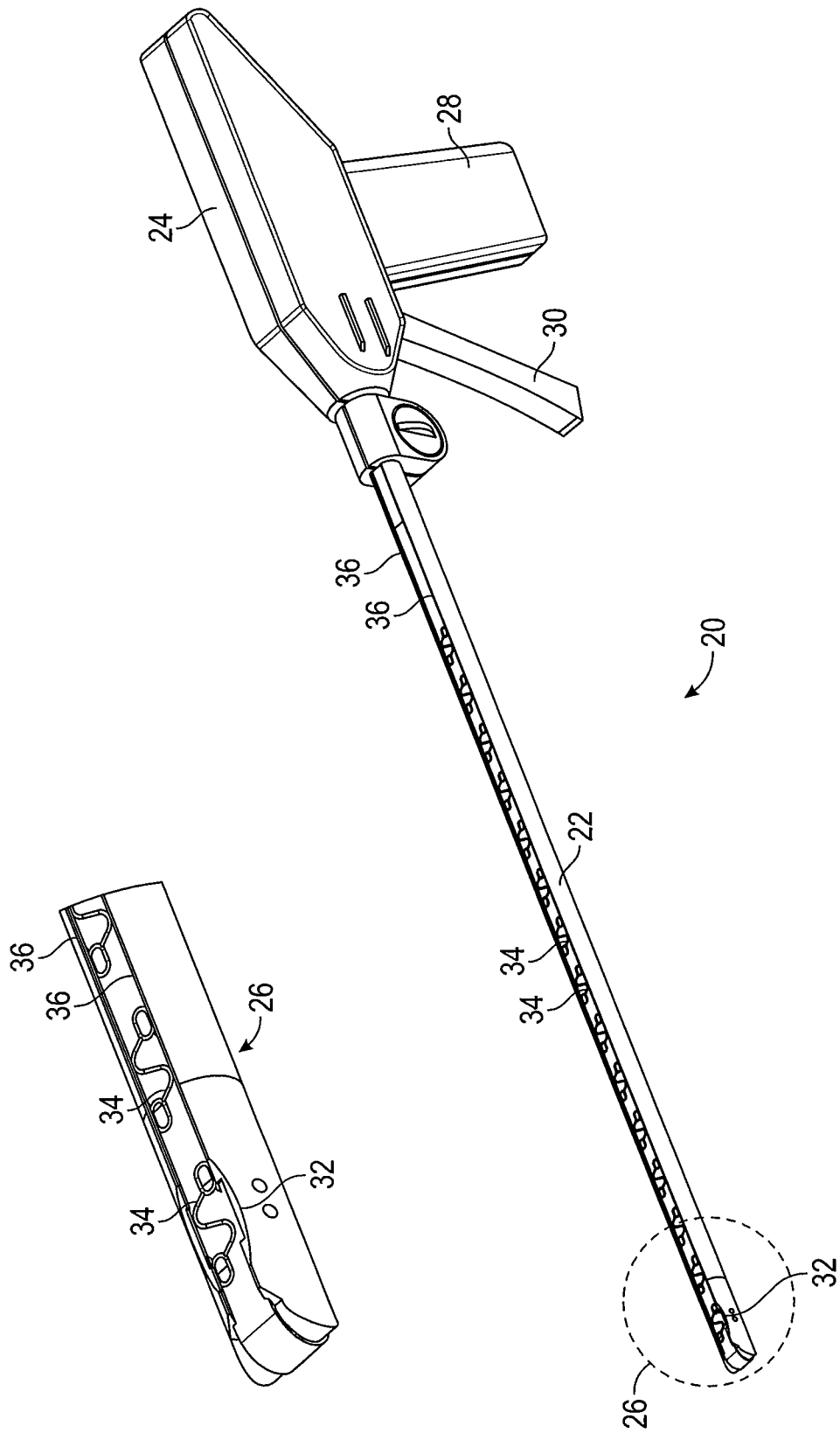
FIG. 1 is a perspective view of a fastening device constructed in accordance with the teachings of the present disclosure.
Figure 2:
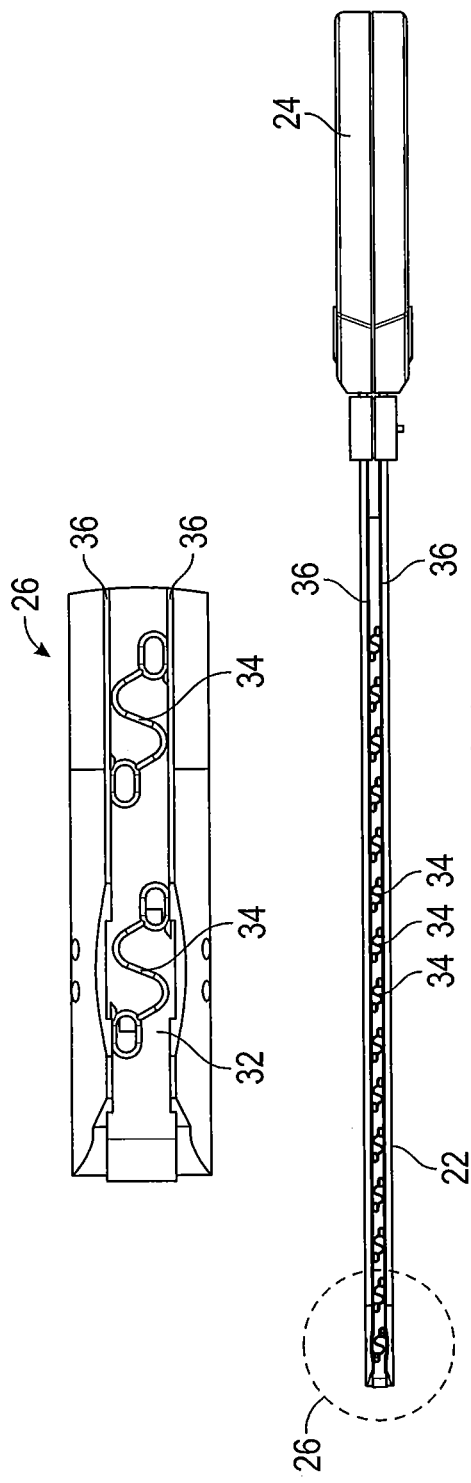
FIG. 2 is a top plan view of the fastening device of FIG. 1.
Figure 3:
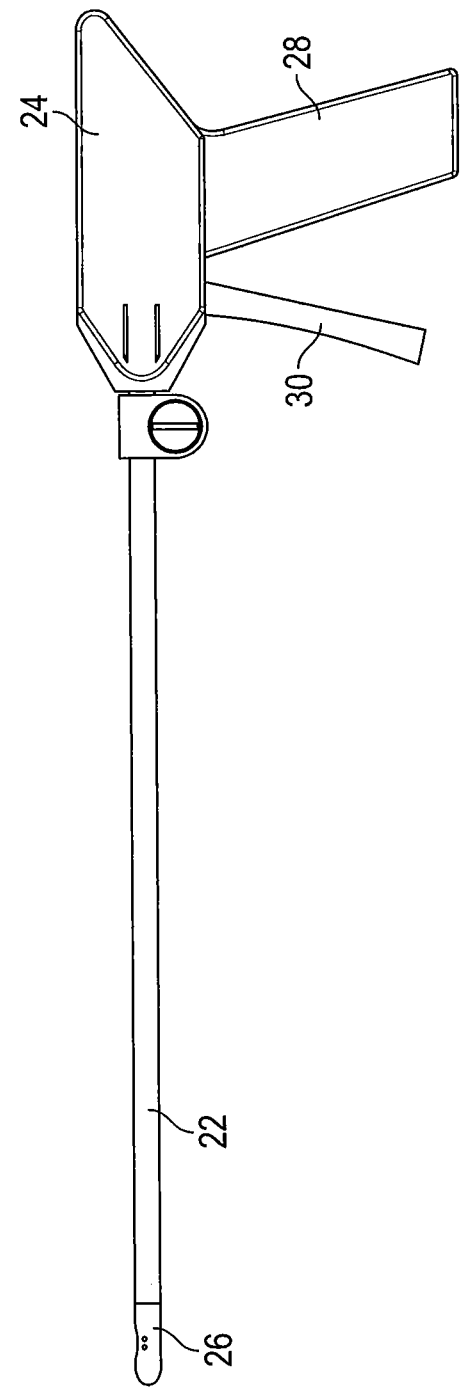
FIG. 3 is a side plan view of the fastening device of FIG. 1.

While the present disclosure is susceptible to various modifications and alternative constructions, certain illustrative embodiments thereof have been shown in the drawings and will be described below in detail. It should be understood, however, that there is no intention to limit the present invention to the specific forms disclosed, but on the contrary, the intention is to cover all modifications, alternative constructions and equivalents falling within the spirit and scope of the present disclosure.

DETAILED DESCRIPTION

Referring now to the drawings, and with specific reference to FIG. 1, a medical fastening device constructed in accordance with the teachings of the present disclosure is generally referred to by reference numeral 20. The medical fastening device 20, as will be described in further detail herein, may advantageously enable convenient yet effective means of providing fasteners within a surgical environment. The disclosed embodiments may additionally facilitate the installation of fasteners during minimally invasive surgical procedures, such as laparoscopic procedures, and the like. As used for laparoscopic treatment of a hernia, for example, the first embodiment of FIGS. 1-7 of the fastening device 20 may be placed under sections of tissue, within or around the abdominal region, to fasten tissues of the abdominal wall or to fasten prosthetic mesh to the abdominal wall from the inside. Although the embodiments disclosed herein demonstrate tissue fastening as applied to laparoscopic applications, it will be understood that the present disclosure may be equally or similarly applied to other medical procedures.

Turning again to FIGS. 1-3, the fastening device 20 may generally include an elongate member 22 which extends between a control end 24 disposed at a proximal end thereof, and a working end 26 disposed at a distal end thereof. The control end 24 may include a grip 28 as well as a compressible trigger 30, or any other suitable means for receiving input from a user and converting the user input into a fastening action that is performed at the working end 26 of the fastening device 20. The working end 26 may be configured with a side-firing aperture 32, or a fastening interface disposed at a longitudinal side thereof, through which fasteners 34 may be installed. Furthermore, one or more of the fasteners 34 may be advanced toward and fed to the side-firing aperture 32 of the working end 26 through guides 36 disposed along one or more longitudinal sections of the elongate member 22.

As shown in more detail in FIGS. 4-7, the working end 26 of the fastening device 20 may at least partially enclose a first arcuate needle 38 and a second arcuate needle 40, each of which may be substantially concealed within the side-firing aperture 32 of the working end 26 in an initial or default position. In particular, the first arcuate needle 38 may be adapted to rotatably or pivotally advance about a first axis 42 in a first direction as indicated by a first arrow 44, and further, rotatably or pivotally retracted in a reverse or opposing direction. Similarly, the second arcuate needle 40 may be adapted to rotatably or pivotally advance about a second axis 46, axially offset from the first axis 42, in a second direction as indicated by a second arrow 48, and further, rotatably or pivotally retracted in a direction opposing the second direction. Additionally, an inner edge of each of the first and second arcuate needles 38, 40 may include a recess 50, such as to form a hook, a groove, a tine, a canted surface, or any other suitable structure configured to receive or engage a fastener 34 therein. Although the embodiments presently shown may depict the arcuate needles 38, 40 with retrograde-type recesses 50, configured to engage a fastener 34 during retraction, it will be understood that other configurations may be equally or similarly employed, such as antegrade-type recesses configured to engage a fastener 34 during needle advancement, or the like. In other modifications, a recess may be provided on the outer edge of each of the first and second arcuate needles 38, 40. In further modifications, the firing aperture of the working end 26 may be configured as an end-firing aperture, an oblique-firing aperture, or in any other suitable configuration.

Figure 4:
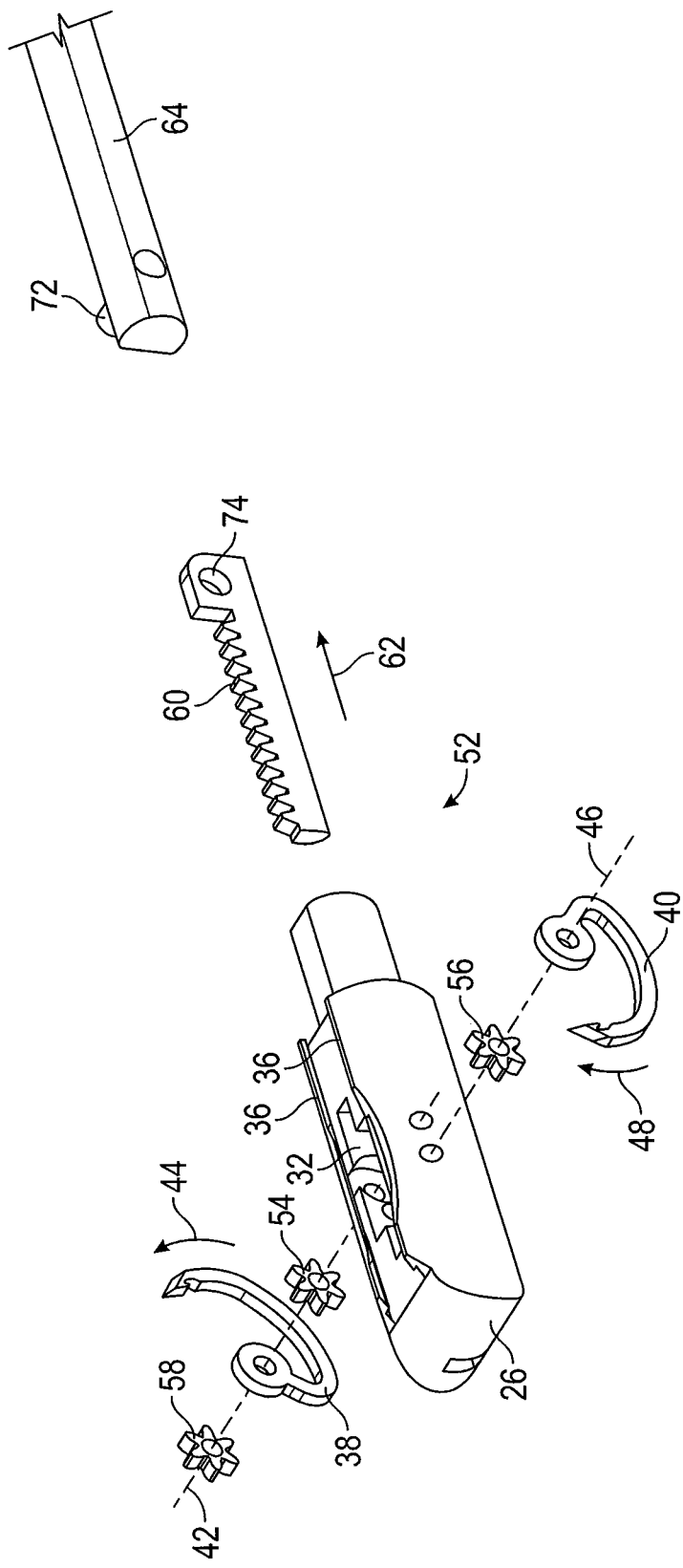
FIG. 4 is an exploded perspective view of the working end of the fastening device of FIG. 1.

Still referring to FIGS. 4-7, the fastening device 20 may further employ at least one drive mechanism 52 that is operatively coupled to each of the first and second arcuate needles 38, 40, and configured to rotatably engage each of the first and second needles 38, 40 between a retracted position and an extended position in response to user input received through the control end 24. As shown in FIG. 4, for example, the drive mechanism 52 may include a first gear 54 that is directly coupled to the first arcuate needle 38, a second gear 56 that is directly coupled to the second arcuate needle 40, and a drive gear 58 that is directly coupled to each of the first arcuate needle 38 and the first gear 54. More particularly, the first gear 54 and the second gear 56 may be axially offset but in rotational alignment and in contact with one another such that a rotation of the first gear 54 directly corresponds to an equal but reverse rotation of the second gear 56, and vice versa. Furthermore, the drive mechanism 52 may include a gear rack 60 that is longitudinally movable and at least partially disposed within the working end 26 and in direct mechanical communication with at least the drive gear 58.

Correspondingly, in the particular embodiments shown in FIGS. 4-7 for example, moving the gear rack 60 in the proximal direction, or toward the control end 24 as indicated by arrow 62, may cause the drive gear 58, and thus the attached first arcuate needle 38 and the first gear 54, to rotate in the counterclockwise direction indicated by arrow 44. Further, as the first gear 54 is rotated, the second gear 56 and the attached second arcuate needle 40 may simultaneously be caused to equally rotate in a reverse or clockwise direction indicated by arrow 48. Alternatively, moving the gear rack 60 in the distal direction, or toward the working end 26, may cause the drive gear 58, and thus the attached first arcuate needle 38 and the first gear 54, to rotate in a clockwise direction, while the second gear 56 and the attached second arcuate needle 40 may be caused to simultaneously and equally rotate in a counterclockwise direction. While only one implementation is provided in the drawings, other possible drive mechanisms and/or other gear configurations will be apparent to those skilled in the art without departing from the scope of the appended claims. For example, in other modifications, the fastening device 20 may employ more than two arcuate needles which, for instance, partially oppose one another, or alternatively, rotate in like manner and direction relative to one another. In alternative modifications, the arcuate needles 38, 40 may be configured to be rotated sequentially rather than simultaneously relative to one another, and/or configured to be rotated at non-identical rates of angular displacement relative to one another. In additional modifications, the arcuate needles 38, 40 may be configured to rotate about a common axis rather than axially offset. In further modifications, the fastening device 20 may provide an arcuate needle that is configured to rotate about an axis that is parallel, or otherwise generally not perpendicular, to the elongate member 22. In still further modifications, the working end 26 of the fastening device 20 may be articulated, such as pivotable or otherwise movable, relative to the elongate member 22 about one or more axes.

Figure 5:
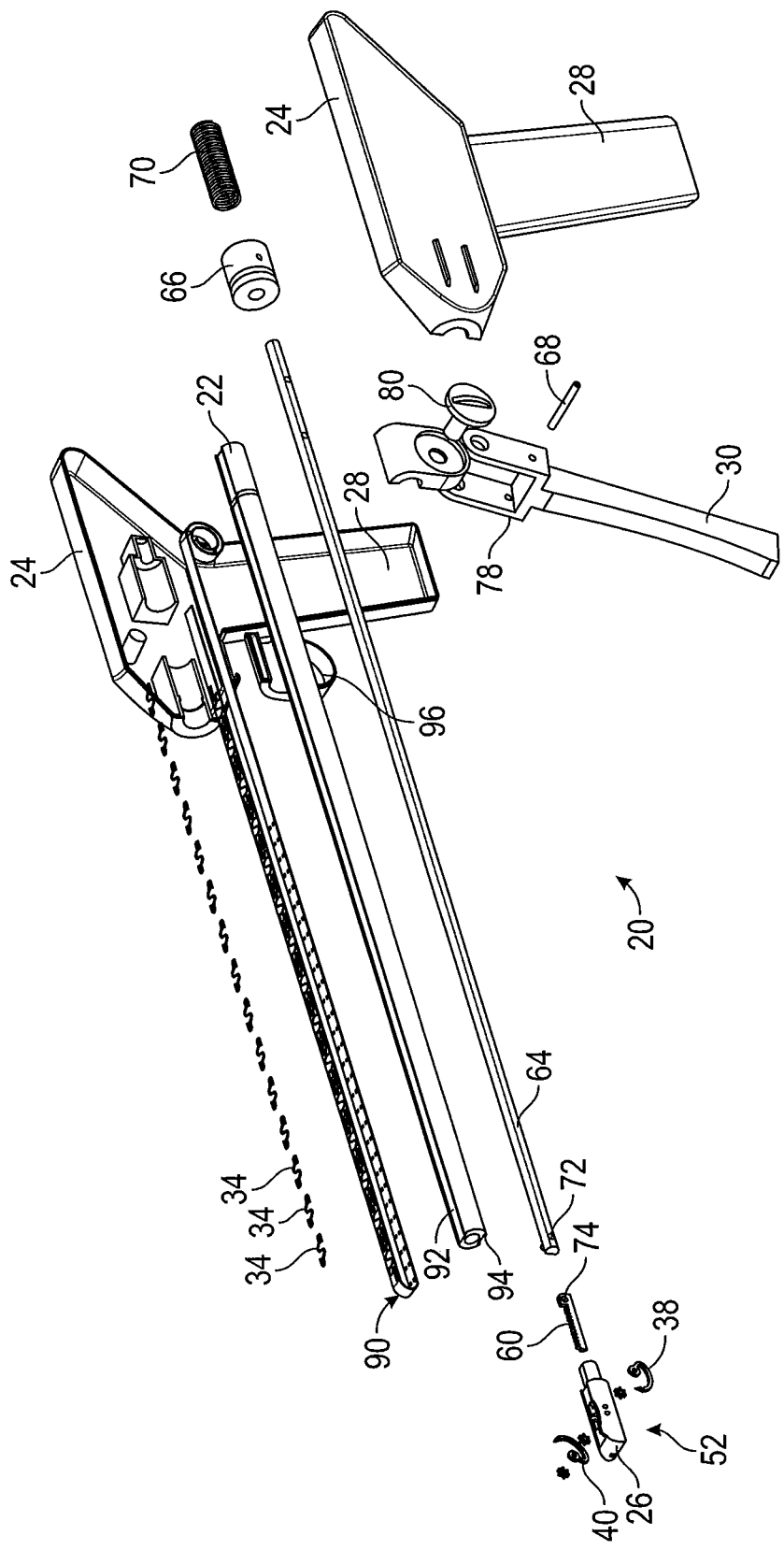
FIG. 5 is an exploded perspective view of the fastening device of FIG. 1.
Figure 6:
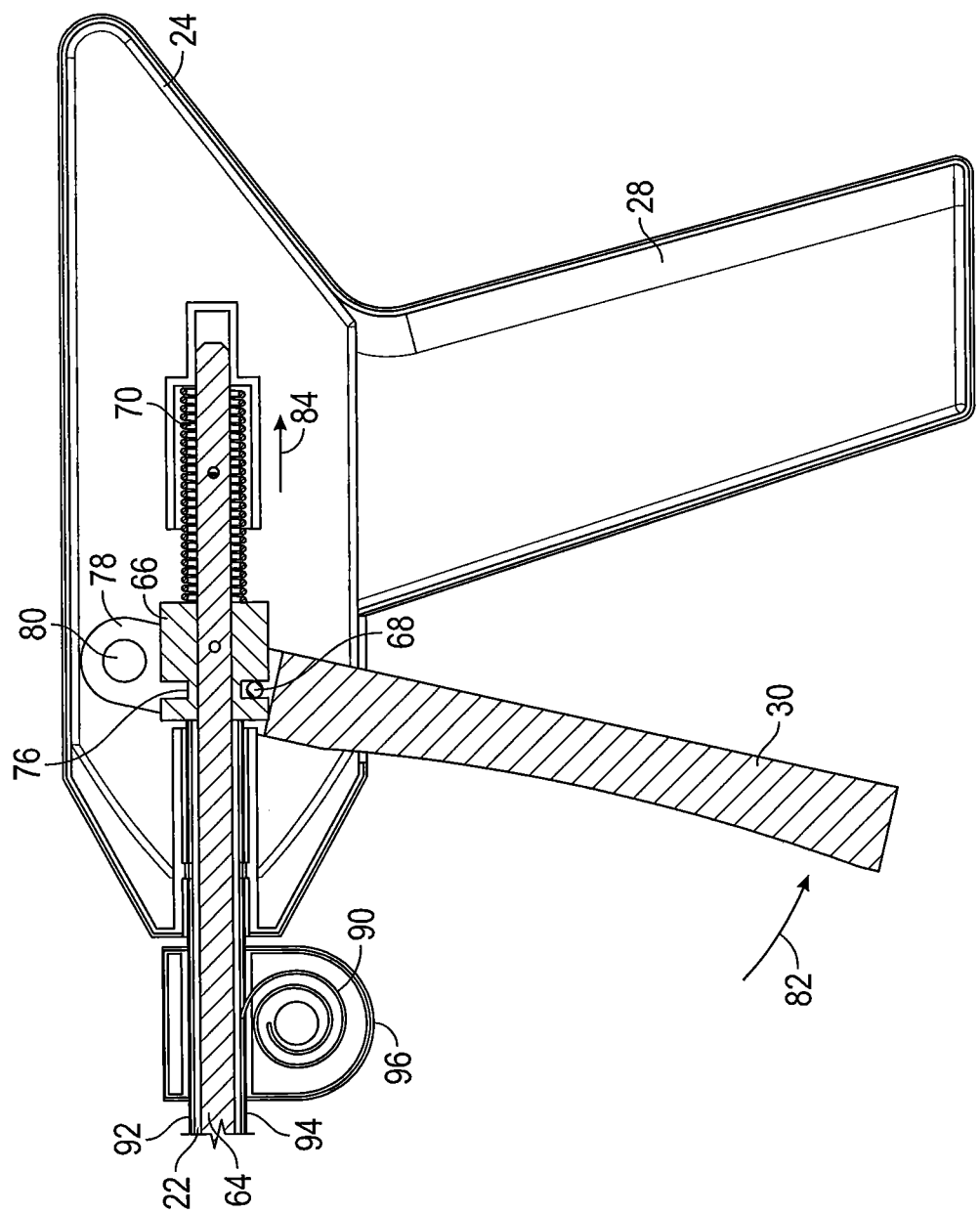
FIG. 6 is a cross-sectional side view of the control end of the fastening device of FIG. 1.
Figure 7:
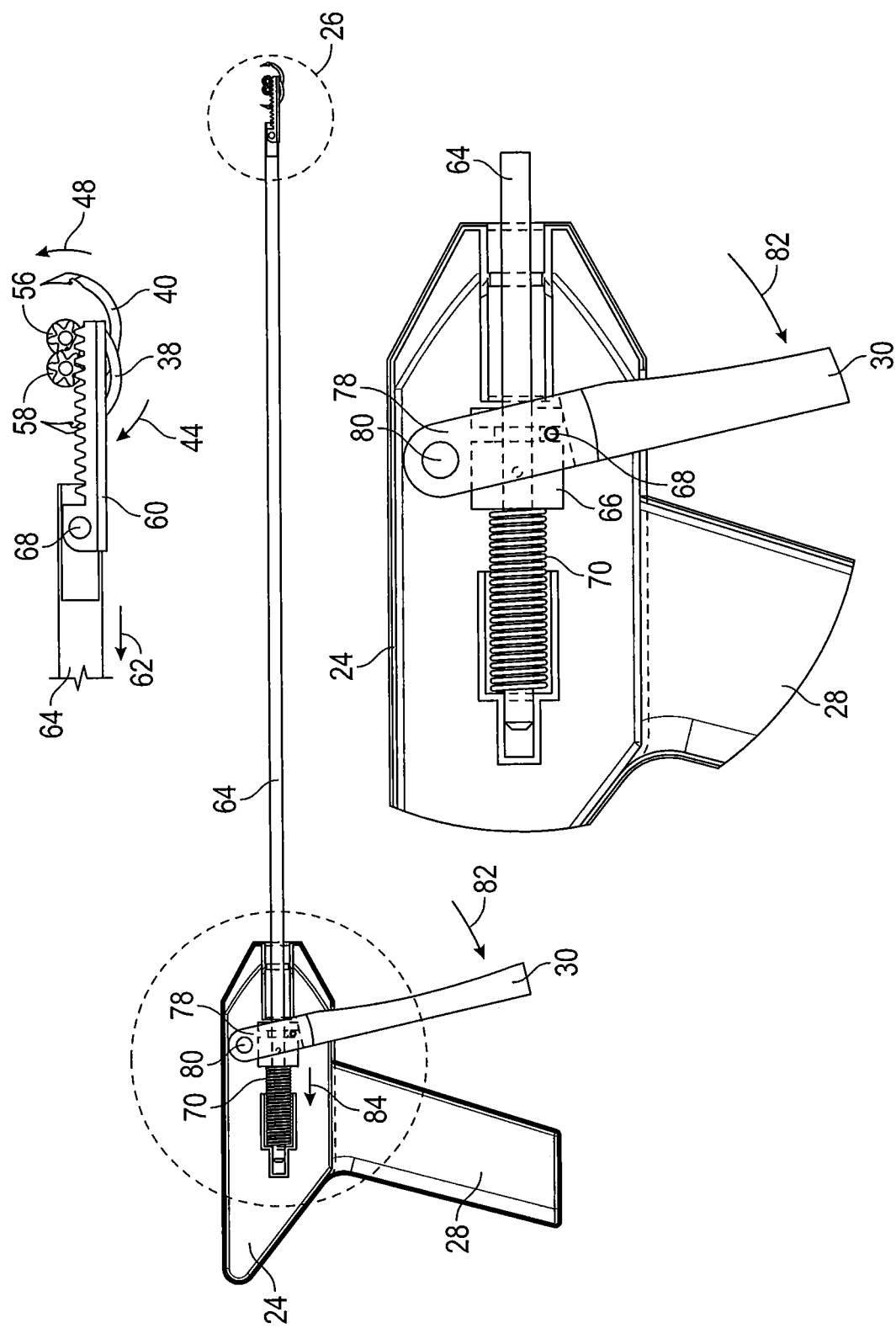
FIG. 7 is a cross-sectional side view of the fastening device of FIG. 1.

The drive mechanism 52 of FIGS. 4-7 may further be adapted and/or expanded upon to accommodate a control end 24 which employs one of any number of different actuation means, including mechanical, electrical, electromechanical, electromagnetic, or any other suitable means for enabling actuation of the drive mechanism 52. As shown in FIGS. 5-7, for example, a control end 24 employing a grip 28 and a compressible trigger 30 may be implemented using, for example, a mechanical assembly of an actuator rod 64, a drive collar 66, a drive pin 68, a compression spring 70, and the like. The actuator rod 64 may be slidably disposed within the elongate member 22 and configured to axially extend between at least the gear rack 60 of the working end 26 and the control end 24. More specifically, a distal end of the actuator rod 64 may be coupled directly to a proximal end of the gear rack 60, for instance, by means of anchoring a rod pin 72 in an aperture 74 of the gear rack 60, or any other suitable means. The drive collar 66 may be coaxially and rigidly coupled to the proximal end of the actuator rod 64 such that all of at least the actuator rod 64, elongate member 22 and the drive collar 66 are able to simultaneously rotate relative to the control end 24. The drive collar 66 may additionally provide a groove 76 that is radially disposed thereabout and configured to partially receive the drive pin 68 therein.

As shown in FIGS. 4-7, the trigger 30 may pivotally couple to the control end 24 through a yoke 78 that is pivotally anchored to the control end 24 across and about a transverse anchor pin 80. The drive pin 68 may also be transversely coupled across the yoke 78 of the trigger 30 in a manner configured to at least partially bias the drive pin 68 against the groove 76 in the drive collar 66 irrespective of the rotational position of the drive collar 66, actuator rod 64 and the elongate member 22. Moreover, the yoke 78 of the trigger 30 may be configured with enough clearance to be sufficiently mounted about the drive collar 66. Additionally, the compression spring 70 may be coaxially disposed about the proximal end of the actuator rod 64 and configured to axially bias the drive collar 66, and thus the actuator rod 64, toward the distal end of the fastening device 20. This default or starting position of the trigger 30 may correspond to the fully retracted needle position, where each of the first and second arcuate needles 38, 40 are tucked within the side-firing aperture 32 of the working end 26.

To actuate the drive mechanism 52, the trigger 30 may be compressed, or caused to pivot toward the grip 28 as shown by arrow 82, which may in turn cause the drive pin 68 to push both the drive collar 66 and the actuator rod 64 toward the proximal end of the fastening device 20. More particularly, as the actuator rod 64 is pulled away from the working end 26, the rod pin 72 at the distal end thereof may likewise pull the gear rack 60 in the proximal direction as previously indicated by arrow 62 in FIG. 4. Furthermore, pulling the gear rack 60 in the direction 62 shown may cause the drive gear 58 to rotate, which in effect, may cause the first and second gears 54, 56 to rotate. As each of the first and second gears 54, 56 rotate, the first and second arcuate needles 38, 40 may be caused to simultaneously and radially extend in the opposing directions 44, 48 shown until a fully extended needle position is reached. Conversely, to reverse the drive mechanism 52, the trigger 30 may be decompressed, or caused to return to its default position. Releasing the trigger 30 may push the drive pin 68, the drive collar 66 and the actuator rod 64 away from the control end 24 and toward the distal end of the fastening device 20, thus relieving and unloading the compression spring 70 to its default state. Furthermore, as the trigger 30 is released, the rod pin 72 of the actuator rod 64 may longitudinally push the gear rack 60 back to its initial position and restore each of the first and second arcuate needles 38, 40 to the default position, or the fully retracted needle position.

Figure 8:
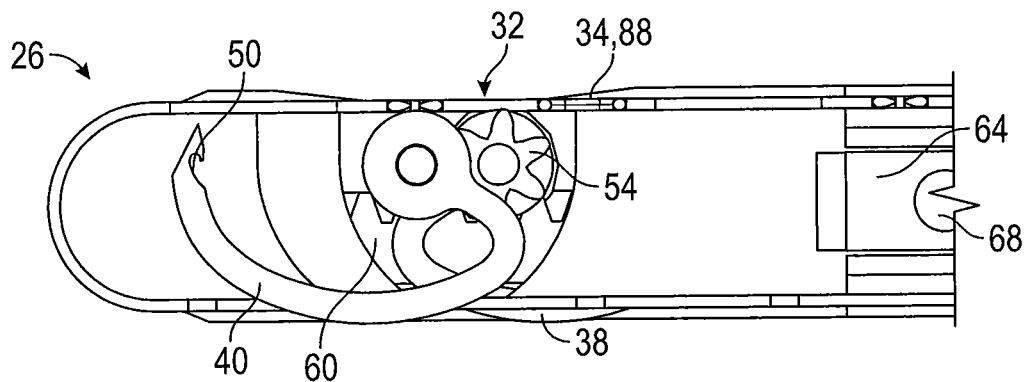
FIGS. 8-10 are partial cross-sectional side views of the working end of the fastening device of FIG. 1 during different stages of deployment.
Figure 9:
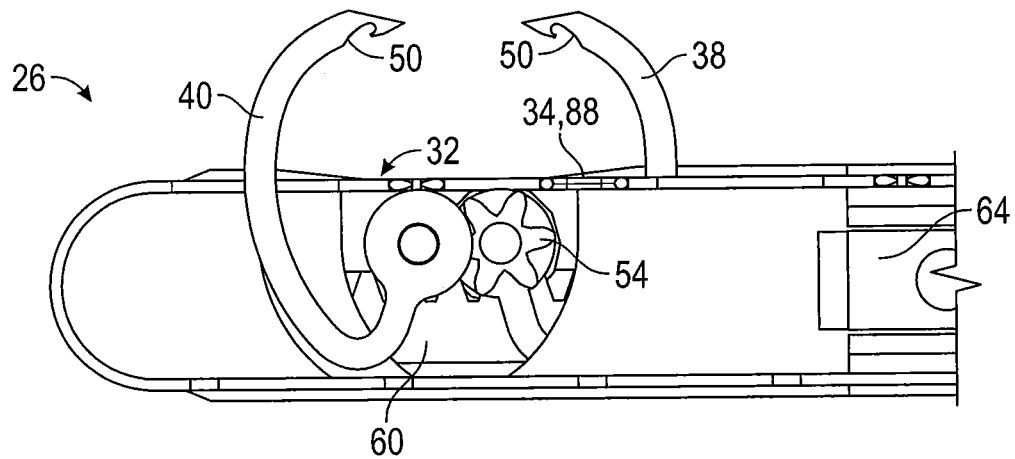
Figure 10:
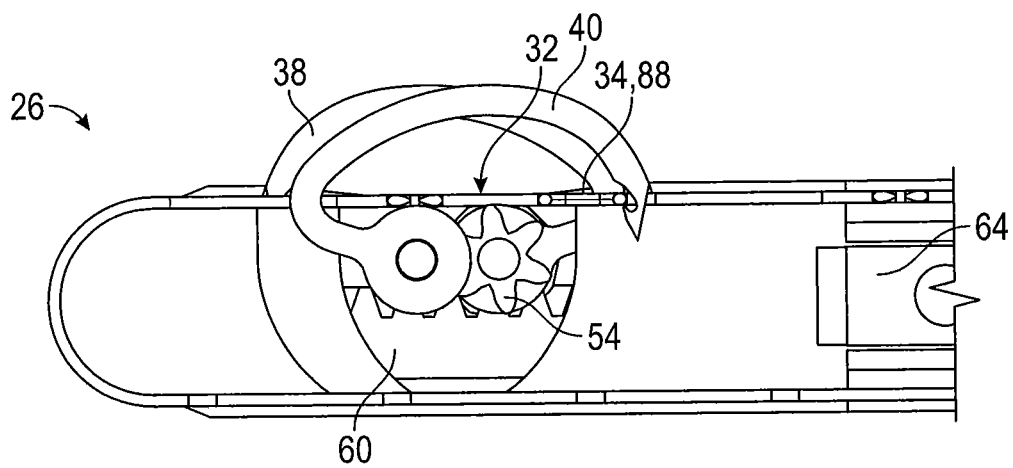
Figure 11:
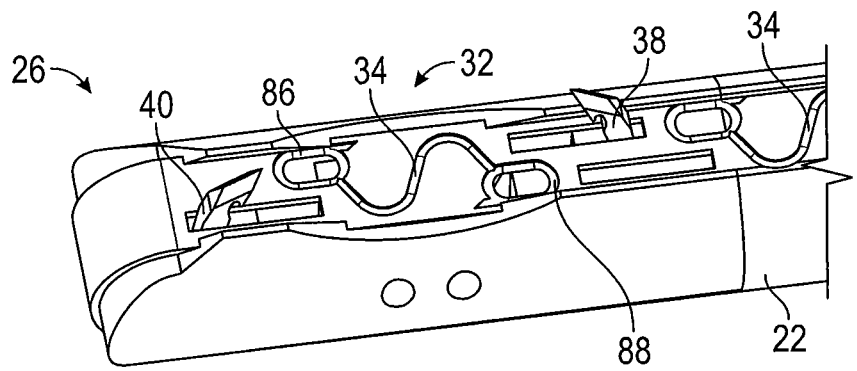
FIGS. 11-13 are perspective views of the working end of the fastening device of FIG. 1 during different stages of deployment.
Figure 12:
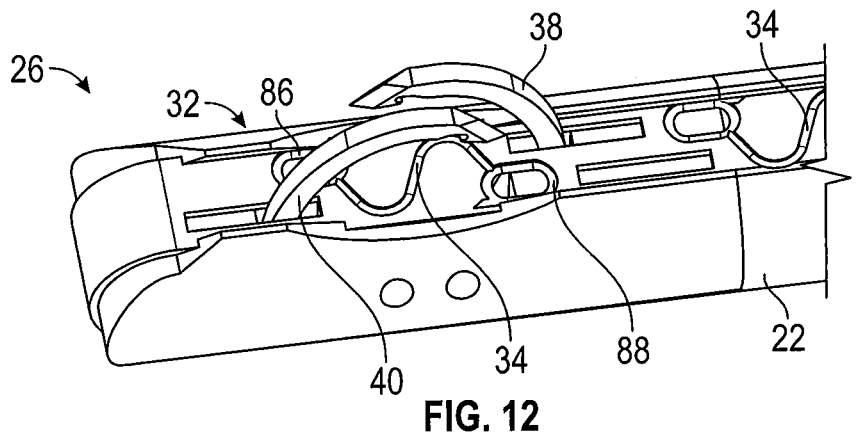
Figure 13:
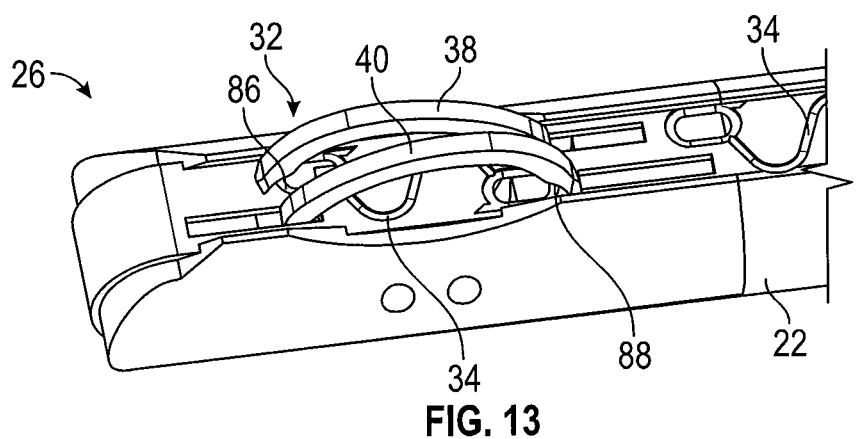

Turning now to FIGS. 8-13, different stages of the advancement of the first and second arcuate needles 38, 40 of the working end 26, for instance, during actuation of the drive mechanism 52 of FIGS. 4-7, are provided. In the default retracted needle position, as shown for example in FIGS. 8 and 11, each of the first and second arcuate needles 38, 40 may be substantially concealed and disposed within and substantially beneath the side-firing aperture 32 of the working end 26. Additionally, one or more fasteners 34 to be installed may be removably retained along the side-firing aperture 32 with ends or needle guides 86, 88 positioned in a manner which facilitates engagement with the first and second arcuate needles 38, 40. During advancement, each of the first and second arcuate needles 38, 40 may be rotatably extended and forwardly advanced, as shown for example in FIGS. 9 and 12, through relevant sections of tissue and/or prosthetic material if applicable. Once in the fully extended needle position, as shown for example in FIGS. 10 and 13, each of the first and second arcuate needles 38, 40 may be positioned to engage the respective needle guides 86, 88 of the fastener 34 to be installed. Specifically, the hook 50 of the first arcuate needle 38 may be engaged with the first end or needle guide 86, and the hook 50 of the second arcuate needle guide 40 may be engaged with the second end or needle guide 88 as shown in FIGS. 10 and 13.

Once securely engaged, the trigger 30, and thus the drive mechanism 52, may be released and disengaged by a user to deploy or install the fastener 34. Upon release, each of the first and second arcuate needles 38, 40 may be caused to retract from the extended needle position of FIGS. 10 and 13, retract through relevant sections of tissue and/or any applicable prosthetic material, and return to the initial retracted needle position of FIGS. 8 and 11 while pulling the respective ends 86, 88 of the fastener 34. Specifically, the hook 50 of the first arcuate needle 38 may retractively pull the engaged first needle guide 86 of the fastener 34 back through the path taken by the first arcuate needle 38, while the hook 50 of the second arcuate needle 40 may retractively pull the second needle guide 88 of the fastener 34 back through the path taken by the second arcuate needle 40, until the first and second arcuate needles 38, 40 reach the fully retracted needle position of FIGS. 8 and 11. Once deployed, the first end 86 of the fastener 34 may be installed at least partially within a section of tissue proximate to the first arcuate needle 38 in its fully retracted needle position, as shown in FIGS. 8 and 11, while the second end 88 of the fastener 34 may be installed at least partially within a section of tissue proximate to the second arcuate needle 40 in its fully retracted needle position. More generally, the fastener 34 may be installed within one or more sections of tissue and/or prosthetic material in a substantially helical configuration, which may in part be maintained by retention elements, or the like, disposed on the ends 86, 88 of the fastener 34. For example, the ends 86, 88 of the fastener 34 may be adapted to facilitate entry thereof into tissue, but also to resist retraction and retain the fastener 34 within the tissue once deployed.

As shown in FIGS. 8-10, the outer circumference of each of the first and second arcuate needles 38, 40 may not necessarily be truly or consistently arcuate, but rather may comprise an obliquely arcuate form. Correspondingly, the path taken by each of the first and second arcuate needles 38, 40 may not necessarily be truly circular. Rather, such a configuration may advantageously enable each of the first and second arcuate needles 38, 40 to maintain a low-profile when in the fully retracted needle position, as shown in FIGS. 8 and 11, while still enabling optimum reach or extension into tissue during advancement, as shown in FIGS. 9 and 12. In this manner, during advancement for example, the first arcuate needle 38 may enter through a first section of tissue and exit through a second section of tissue, while the second arcuate needle 40 may simultaneously enter through the second section of tissue and exit through the first section of tissue. Conversely, during release and retraction, the first arcuate needle 38 may retract back through the second section of tissue and exit, in reverse, through the first section of tissue, while the second arcuate needle 40 may simultaneously retract back through the first section of tissue and exit, in reverse, through the second section of tissue. Furthermore, each arcuate needle 38, 40 may be shaped and/or otherwise configured to rotate in a cammed fashion such that, it creates a progressively tighter pull as it travels through the tissue, and thus, creates a tighter fastening of the tissue.

Figure 14:
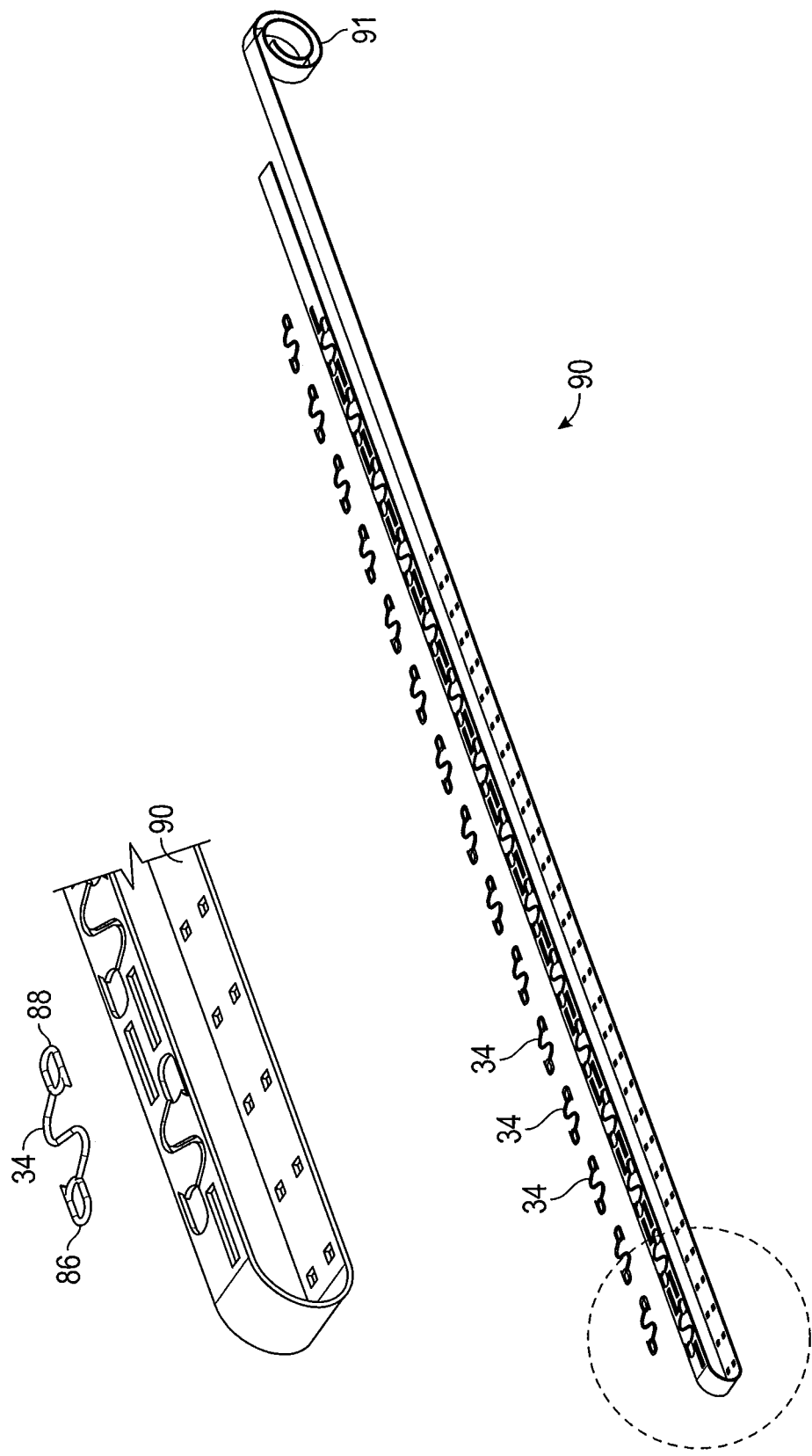
FIG. 14 is a perspective view of a ribbon cartridge of fasteners for use with the fastening device of FIG. 1.

Referring back to FIGS. 5-6 as well as FIG. 14, the fastening device 20 may further include one or more fasteners 34 to be installed, for example, as a cartridge, string, ribbon 90, or any other suitable collection of deployable fasteners 34. In the embodiment of FIGS. 5-6 and 14 for example, a ribbon 90 of fasteners 34 may be longitudinally disposed between the guides 36 and along the elongate member 22 generally extending at least from the control end 24 to the distal end of the working end 26. More particularly, the elongate member 22 may be provided with a feed path 92 configured to feed new segments of ribbon 90 holding fasteners 34 to be installed toward the side-firing aperture 32 of the working end 26, as well as a return path 94 configured to return used segments of ribbon 90 toward a return roll 91, or the like, disposed at the control end 24. Furthermore, the fastening device 20 may be configured such that spent ribbons 90 are replaceable and new ribbons 90 can be removably installed or inserted into a compartment 96 thereof. Accordingly, the compartment 96 may be positioned such that the ribbon 90 contained therein is appropriately aligned with the feed path 92 and/or the return path 94 of the elongate member 22. For example, as shown in FIGS. 5-6 and 14, the compartment 96 may be coupled directly to the elongate member 22, and further, allowed to axially rotate therewith so as to maintain alignment between the ribbon 20 and the feed and return paths 92, 94.

Figure 15:
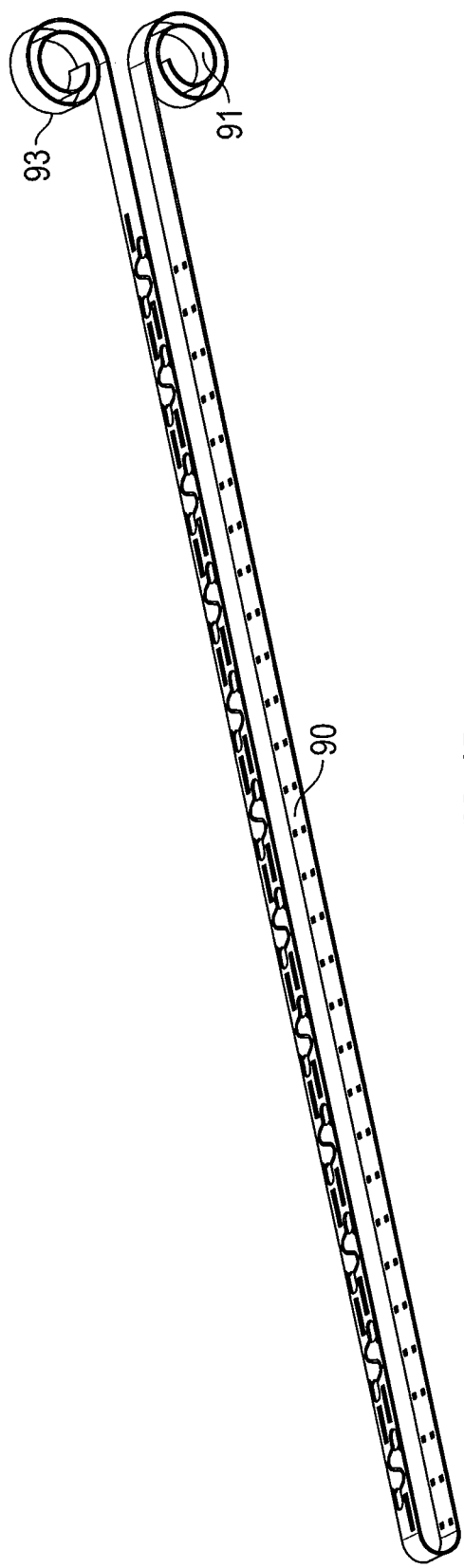
FIGS. 15-16 are perspective views of alternative ribbon cartridges of fasteners.
Figure 16:
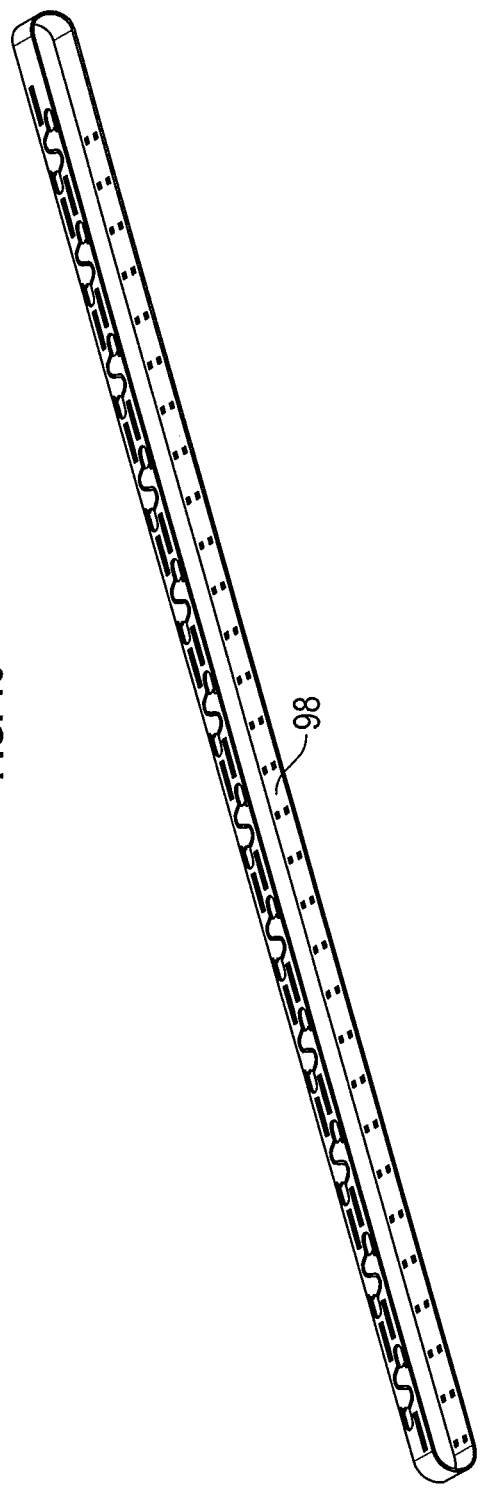

In one possible modification, as shown in FIG. 15 for example, the ribbon 90 of FIG. 14 may further incorporate a feed roll 93 configured to extend the number of fasteners 34 that are available for deployment and preloaded into the fastening device 20. For instance, the feed roll 93 may be housed within a compartment of the fastening device 20 and coupled to the feed path 92 to be incrementally fed toward the working end 26 thereof. In addition, the fasteners 34 may be provided as a continuous ribbon 98 of fasteners 34 as shown in FIG. 16. In addition, the ribbons 90, 98 may be configured such that each fastener 34 is retained therealong and removable upon engagement by, for example, the first and second arcuate needles 38, 40. Each fastener 34 may also be spaced and positioned on the respective ribbons 90, 98 such that the ends or needle guides 86, 88 thereof are appropriately aligned and engageable with the corresponding first and second arcuate needles 38, 40. The fastening device 20, the drive mechanism 52, the ribbons 90, 98 and/or the compartment 96 may further be configured to incrementally advance the ribbons 90, 98 in a manner which positions a new fastener 34 appropriately over the side-firing aperture 32 and the first and second arcuate needles 38, 40. The ribbons 90, 98 may further be advanced manually, semi-automatically or automatically.

Figure 17:
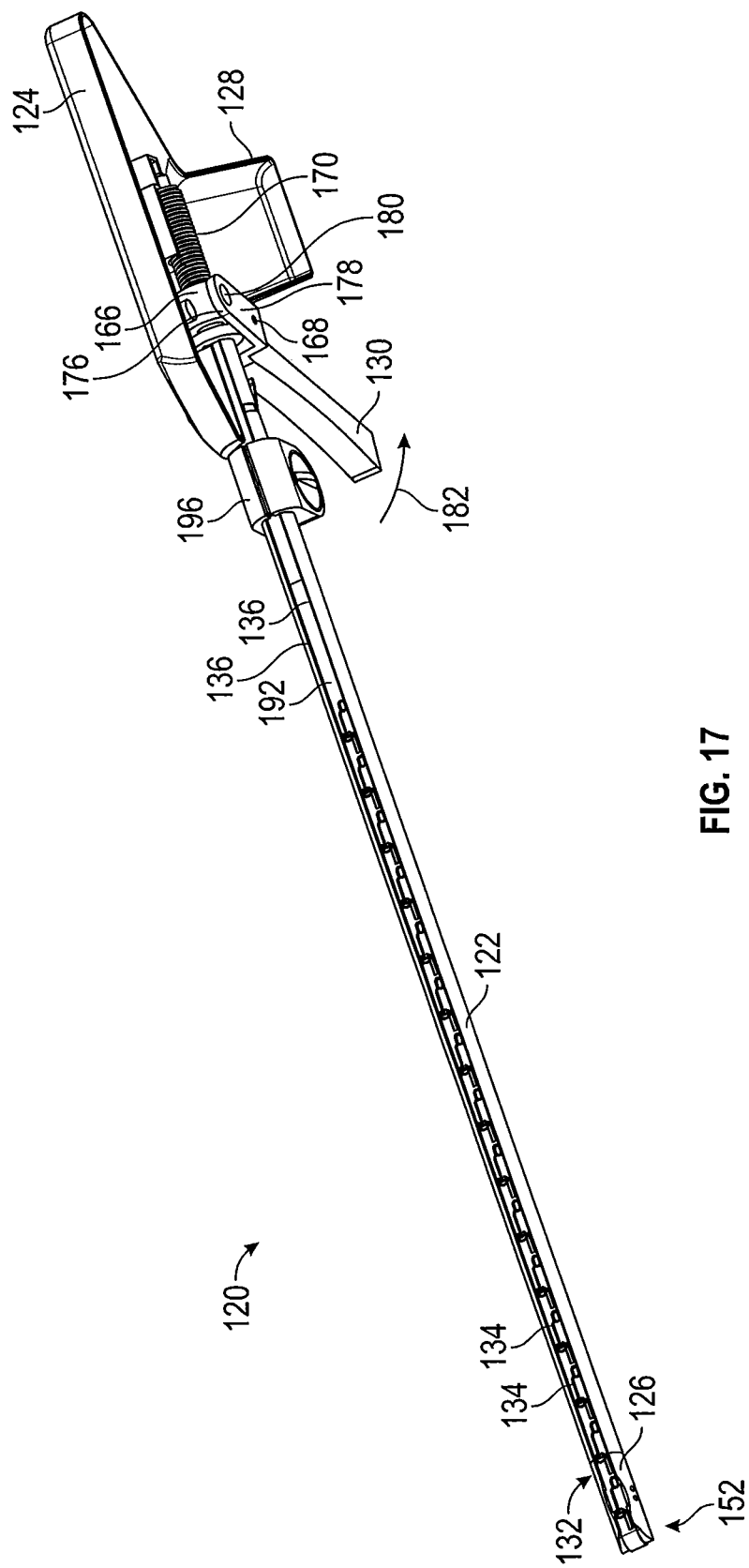
FIG. 17 is a perspective view of another fastening device constructed in accordance with the teachings of the present disclosure.
Figure 18:
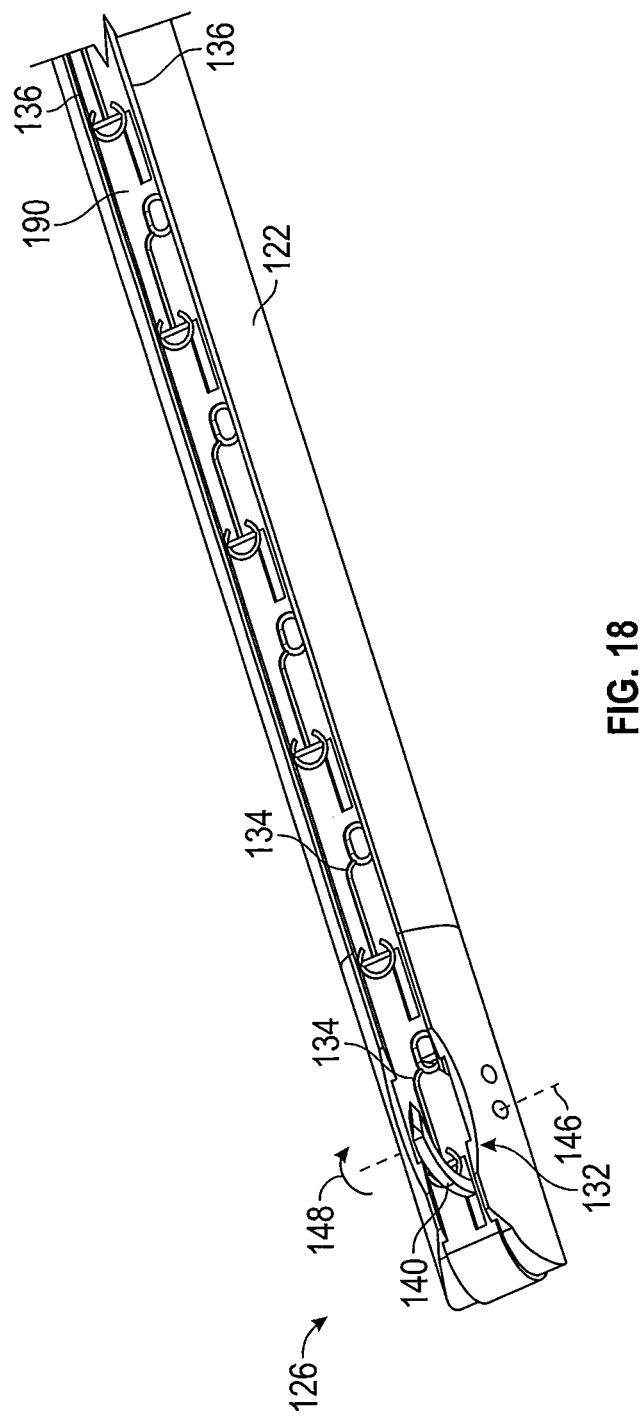
FIG. 18 is a perspective view of the working end of the fastening device of FIG. 17.
Figure 19:
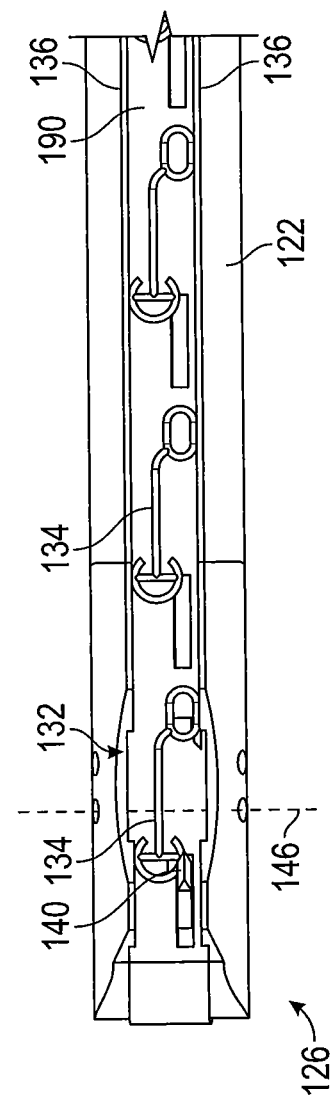
FIG. 19 is a top plan view of the working end of the fastening device of FIG. 17.

Turning now to FIGS. 17-19, further alternative embodiments of a medical fastening device 120 is provided. Similar to the embodiments of FIGS. 1-7, the fastening device 120 may generally include an elongate member 122 extending between a proximally disposed control end 124, and a distally disposed working end 126. Although the control end 124 is shown to include a grip 128 and a trigger 130 that is compressible thereagainst, the control end 124 may employ any other suitable means for receiving input from a user and actuating the fastening device 120 in response to user input. As in previous embodiments, the working end 126 may be configured with a side-firing aperture 132, or a fastening interface disposed at a longitudinal side thereof, through which fasteners 134 may be installed. Furthermore, one or more of the fasteners 134, as dispensed as a ribbon 190 of fasteners 134 from a proximally disposed compartment 196 for instance, may be advanced toward and fed to the side-firing aperture 132 of the working end 126 through guides 136 disposed along one or more longitudinal sections the elongate member 122. In other modifications, the firing aperture of the working end 126 may be configured as an end-firing aperture, an oblique-firing aperture, or in any other suitable configuration. In still further modifications, the working end 126 of the fastening device 20 may be articulated, such as pivotable or otherwise movable, relative to the elongate member 122 about one or more axes.

As shown more particularly in FIGS. 18-19, the working end 126 of the fastening device 120 may be implemented using a single-needle configuration, for example, at least partially enclosing a single arcuate needle 140 which may be substantially concealed within the side-firing aperture 132 of the working end 126 while in a default or fully retracted needle position. Similar to the second arcuate needle 40 in previous embodiments, the arcuate needle 140 of FIGS. 18-19 may be advanced through one or more sections of tissue by rotating or pivoting about a transverse axis 146 in a first direction as indicated by a first arrow 148, and correspondingly, be rotatably or pivotally retracted from the one or more sections of tissue in a reverse or opposing direction. Additionally, an inner edge of the arcuate needle 140 may include a recess 150, such as to form a hook, a groove, a tine, a canted surface, or any other suitable structure configured to receive or engage a fastener 134 therein. Although the embodiments presently shown may depict the arcuate needle 140 with retrograde-type recesses 150, for instance, configured to engage a fastener 134 during retraction, it will be understood that other configurations may be equally or similarly employed, such as antegrade-type recesses configured to engage a fastener 134 during needle advancement. In still further modifications, a recess may be provided on the outer edge of the arcuate needle 140.

Still referring to FIGS. 17-19, the fastening device 120 may further employ a drive mechanism 152 similar to the drive mechanism 52 employed in previous embodiments. Although not shown in detail, the drive mechanism 152 may likewise be operatively coupled to the arcuate needle 140 and configured to rotatably engage the arcuate needle 140 between a retracted position and an extended position in response to user input received at the control end 124. In particular, the drive mechanism 152 may be configured such that compression of the trigger 130 in the direction indicated by arrow 182 causes the arcuate needle 140 to advance, for example, through relevant sections of tissue and/or any applicable prosthetic material, in the rotational direction 144 shown until reaching a fully extended needle position. Moreover, the fully extended needle position may directly correspond to the fully compressed position of the trigger 130 relative to the grip 128. Furthermore, the drive mechanism 152 may be configured such that release of the trigger 130, in a direction opposite to the direction indicated by arrow 182, causes the arcuate needle 140 to retract, for example, from relevant sections of tissue, in a direction opposite to the direction indicated by arrow 148, until reaching a fully retracted needle position. The fully retracted needle position may directly correspond to the fully released position of the trigger 130 relative to the grip 128. The drive mechanism 152 of FIGS. 17-19 may be implemented using gear racks and gear sets or any other suitable mechanisms for enabling control of the arcuate needle 140 via the control end 124 of the fastening device 120. In other modifications, the fastening device 120 may employ an arcuate needle configured to extend and rotate in the manner similar to the first arcuate needle 38 of the fastening device 20 of FIG. 1 for instance. In additional modifications, the fastening device 120 may provide an arcuate needle that is configured to rotate about an axis that is parallel, or otherwise generally not perpendicular, to the elongate member 122.

Furthermore, the drive mechanism 152 of FIGS. 17-19 may be adapted to accommodate a control end 124 employing any combination of actuation means, including mechanical, electrical, electromechanical, electromagnetic, and the like. The control end 124 of FIG. 17 employing the grip 128 and the trigger 130 may be implemented using, for example, an assembly of drive collars 166, drive pins 168, compression springs 170, and the like, as in previous embodiments. Moreover, the drive collar 166 may be coupled to the drive mechanism 152 of the working end 126 such that all of at least the elongate member 122 and the drive collar 166 are able to simultaneously rotate relative to the control end 124. The drive collar 166 may additionally provide a groove 176 that is radially disposed thereabout and configured to partially receive the drive pin 168 therein. The trigger 130 may pivotally couple to the control end 124 through a yoke 178 that is pivotally anchored to the control end 124 across and about a transverse anchor pin 180. The drive pin 168 may also be transversely coupled across the yoke 178 of the trigger 130 in a manner configured to at least partially bias the drive pin 168 against the groove 176 in the drive collar 166 irrespective of the rotational position of the drive collar 166 and the elongate member 122. In particular, the yoke 178 of the trigger 130 may be configured with enough clearance to be sufficiently mounted about the drive collar 166. Additionally, the compression spring 170 may be coaxially disposed in relation to the elongate member 122 and configured to axially bias the drive collar 166, and thus the arcuate needle 140, toward a default fully retracted needle position.

Figure 20:
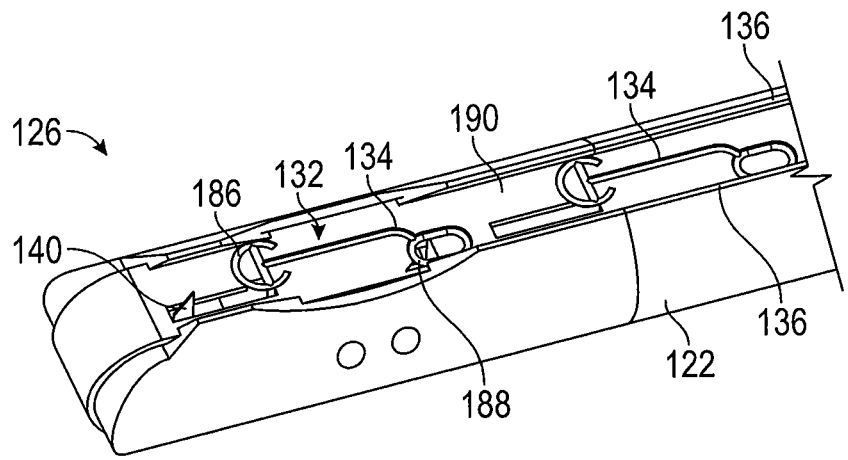
FIGS. 20-22 are perspective views of the working end of the fastening device of FIG. 17 during different stages of deployment.
Figure 21:
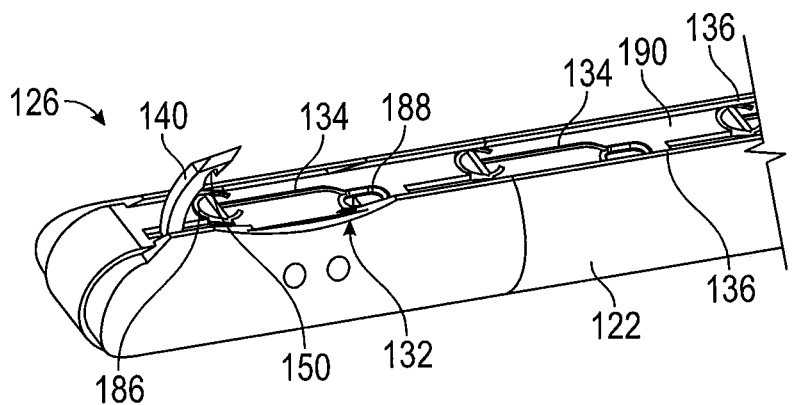
Figure 22:
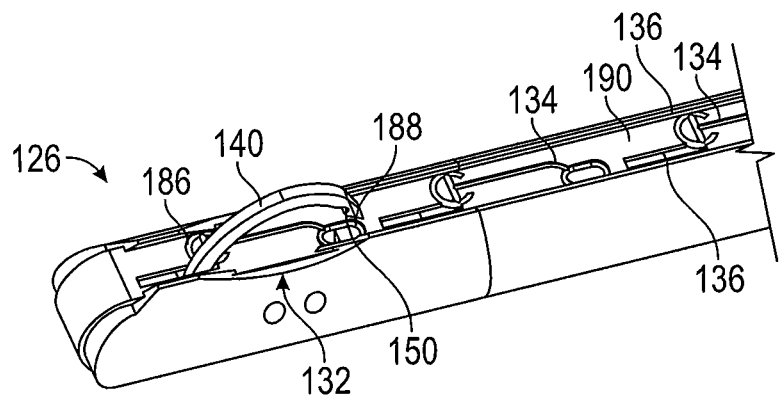
Figure 23:
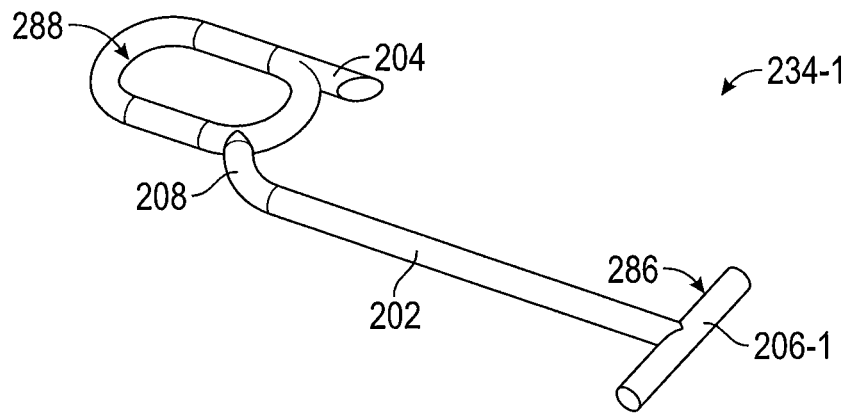
FIGS. 23-28 are perspective views of variations of a fastener having a nonlinear filament segment and a needle guide with a single retention element configured for use with a single-needle fastening device.

Referring now to FIGS. 20-22, different stages of the advancement of the arcuate needle 140 of the working end 126, for instance, during actuation of the drive mechanism 152, are provided. In the retracted needle position, as shown for example in FIG. 20, the arcuate needle 140 may be substantially concealed and disposed within and substantially beneath the side-firing aperture 132 of the working end 126. Additionally, one or more fasteners 134 to be installed may be removably retained along the side-firing aperture 132 with ends 186, 188 positioned in a manner which facilitates the engagement with the arcuate needle 140. During advancement, the arcuate needle 140 may be rotatably and forwardly advanced, as shown for example in FIGS. 21-22, through relevant sections of tissue. Once in the fully extended needle position, the arcuate needle 140 may be positioned to engage the leading end or the needle guide 188 of the fastener 134 to be installed. Upon engaging the needle guide 188, the trigger 130 may be released by the user to install the fastener 134, during which the arcuate needle 140 may retract from the extended needle position, retract through relevant sections of tissue, and return to the initial retracted needle position of FIG. 20 while pulling the leading end or needle guide 188 of the fastener 134 therewith. Once deployed, the fastener 134 may generally be installed within one or more sections of tissue and/or a prosthetic material, which may in part be maintained by retention members, retention elements, or the like, disposed on one or more of the ends 186, 188 of the fastener 134. For example, the ends 186, 188 of the fastener 134 may be adapted to facilitate entry thereof into tissue, but also to resist retraction and retain the fastener 134 within the tissue in its deployed form.

Turning now to FIGS. 23-40, exemplary embodiments of various tissue fasteners 234, 334, 434 that may be used with, for example, the single-needle type medical fastening device 120 of FIGS. 17-22, is provided. As shown, each of the fasteners 234, 334, 434 may generally include an elongated filament 202, 302, 402 which extends between a leading end 288, 388, 488 and a trailing end 286, 386, 486. The leading end 288, 388, 488 may take the form of a needle guide configured to interface or engage with a recess or hook 150 of an arcuate needle 140, or the like. In particular, each of the needle guides 288, 388, 488 may take the form of a loop, a circle, an ellipse, an oval, a polygon, or any other suitable form that is engageable by an arcuate needle 140 during deployment. Additionally, each of the needle guides 288, 388, 488 may include at least one retention element 204, 304, 404 disposed thereon and tangentially extending therefrom in a manner configured to resist retraction through tissue once installed. The retention elements 204, 304, 404 may generally include one or more of a tine, a fin, a canted element, or the like. Moreover, the needle guides 288, 388, 488 and the retention elements 204, 304, 404 may be configured to facilitate advancement thereof through sections of tissue while also resisting retraction thereof. Still further, the trailing ends 286, 386, 486 of the fasteners 234, 334, 434 may generally include retention members 206, 306, 406 configured to resist advancement through sections of tissue. For instance, each retention member 206, 306, 406 may include at least one outwardly extending element which lies within a plane that is coplanar with, or otherwise intersecting with, the plane of the respective needle guide 288, 388, 488, or any combination thereof.

Specifically, according to the embodiments of FIGS. 23-28, each of the fasteners 234 shown may provide an elongated filament 202 that is generally linear, but also includes one or more nonlinear segments 208 therealong. For example, as shown in FIGS. 23-28, the elongated filament 202 may include a curved, nonlinear segment 208 disposed between the filament 202 and the leading end or needle guide 288 thereof. Among other advantages, such a configuration may serve to aid with, for example, engagement with an arcuate needle 140, as well as positioning of the fastener 234 with respect to a side-firing aperture 132 associated with the arcuate needle 140. Furthermore, each of the needle guides 288 of the embodiments of FIGS. 23-28 may generally take the form of a loop having only one retention element 204 tangentially extending therefrom. Moreover, the retention element 204 may take the form of a canted element that is configured to resist retraction of the fastener 234 upon deployment.

In comparison to the fasteners 234 of FIGS. 23-28, each of the fasteners 334 of FIGS. 29-34 may provide a purely linear elongated filament 302 with no nonlinear segments, but may otherwise provide a similar configuration for the leading end or needle guide 388 thereof. More specifically, each needle guide 388 of FIGS. 29-34 may generally take the form of a loop having only one canted retention element 304 tangentially extending therefrom configured to resist retraction of the fastener 334 upon deployment. In still a further comparison, each of the fasteners 434 of FIGS. 35-40 may provide a purely linear elongated filament 405 with no nonlinear segments as in the fasteners 334 of FIGS. 29-34, as well as a needle guide 488 that is generally in the shape of a loop as in fasteners 234, 334 of FIGS. 23-34. However, in contrast, each of the fasteners 434 may provide a needle guide 488 having two canted retention elements 404 tangentially extending therefrom. Moreover, both retention elements 404 may be directed away from the leading end 488 and toward the trailing end 486 so as to resist retraction of the fastener 434.

Figure 24:
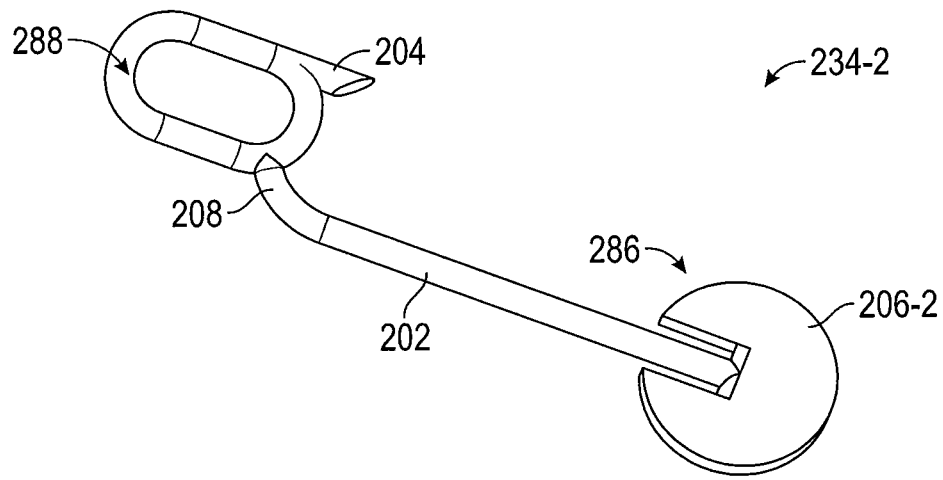
Figure 25:
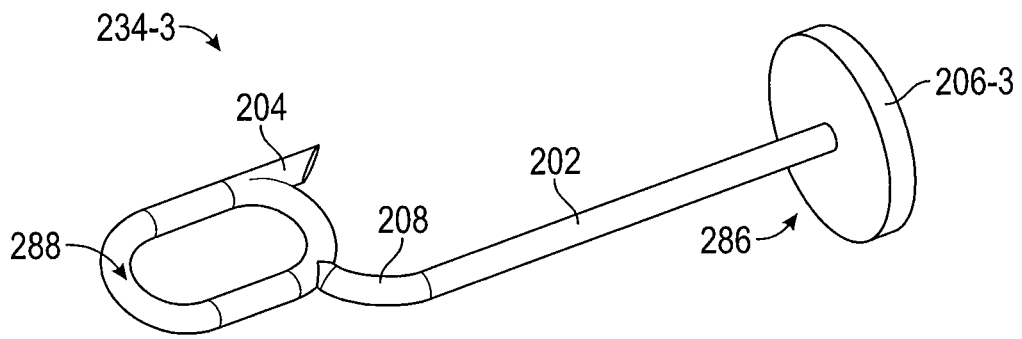
Figure 30:
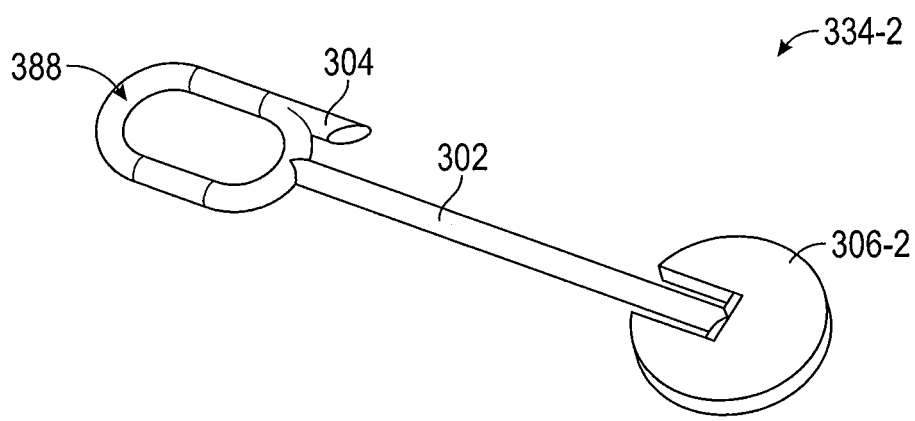
Figure 31:
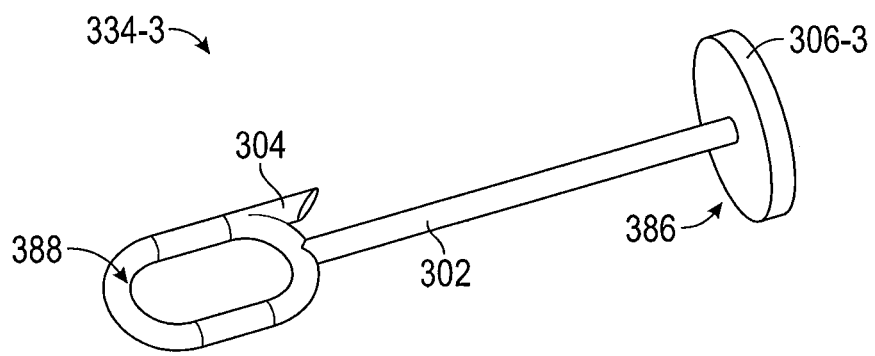
Figure 36:
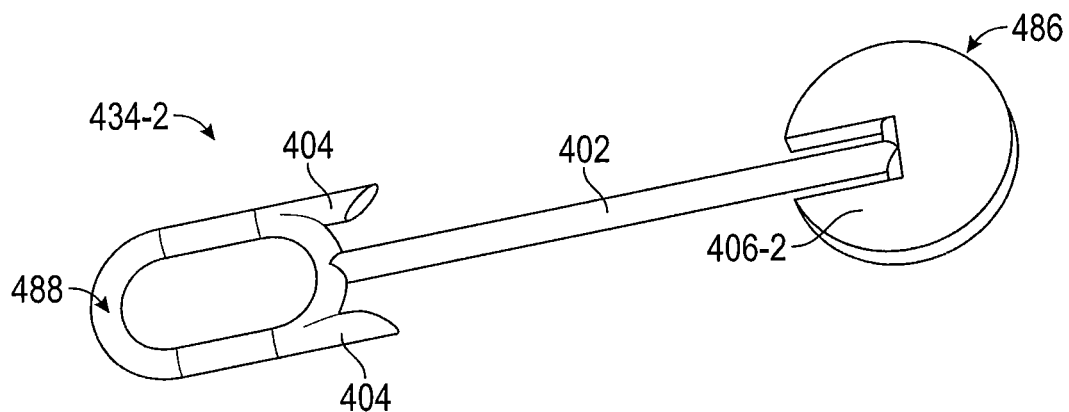
Figure 37:
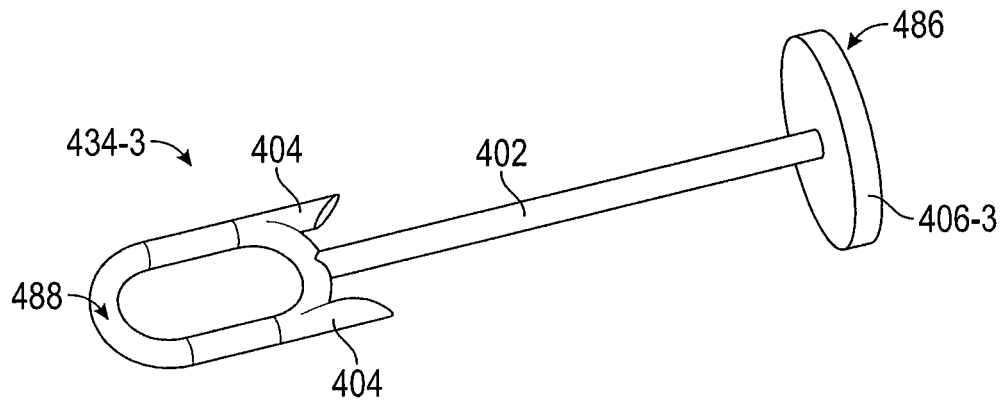

The fasteners 234, 334, 434 of FIGS. 23-40 may further be varied, for example, through modification of the retention members 206, 306, 406 thereof. As shown for instance in FIGS. 23, 29 and 35, each of the retention members 206-1, 306-1, 406-1 may provide transversely extending linear elements which generally lie within a plane that is coplanar to that of the respective fastener 234-1, 334-1, 434-1. In FIGS. 24, 30 and 36, each of the retention members 206-2, 306-2, 406-2 may provide a coplanar, disk-like element with inwardly disposed slots configured to resist further advancement of the fastener 234-2, 334-2, 434-2. In FIGS. 25, 31 and 37, each of the retention members 206-3, 306-3, 406-3 may provide a disk which radially extends from the trailing end 286, 386, 486 of the fastener 234-3, 334-3, 434-3. In contrast to other embodiments, each of the retention members 206-3, 306-3, 406-3 of FIGS. 25, 31 and 37 may lie within a plane that is perpendicular to that of the fastener 234-3, 334-3, 434-3.

Figure 26:
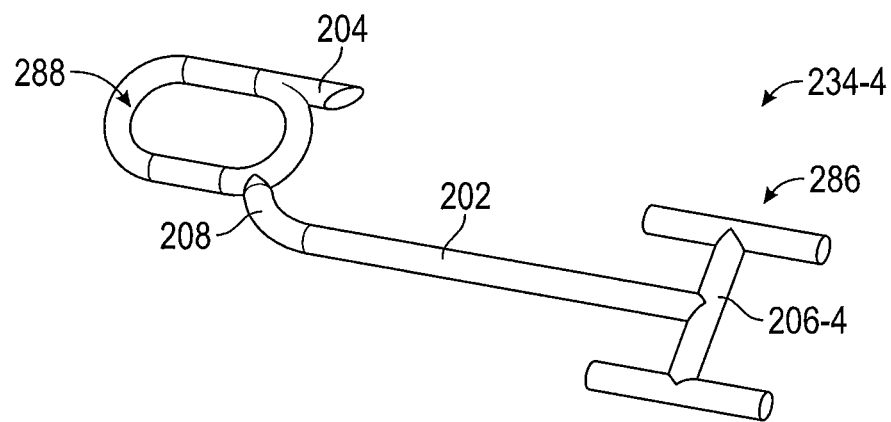
Figure 27:
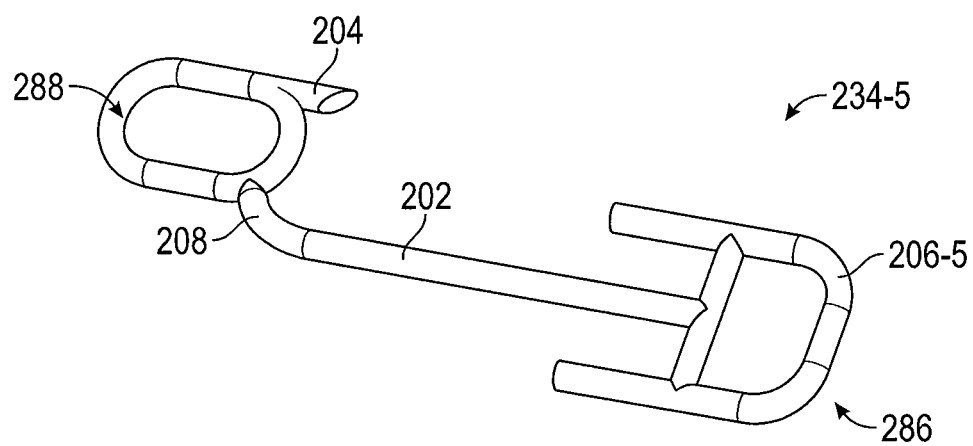
Figure 28:
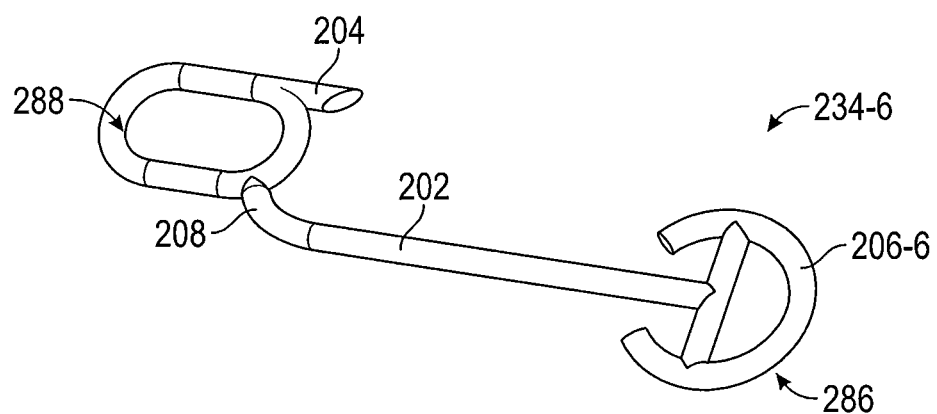
Figure 29:
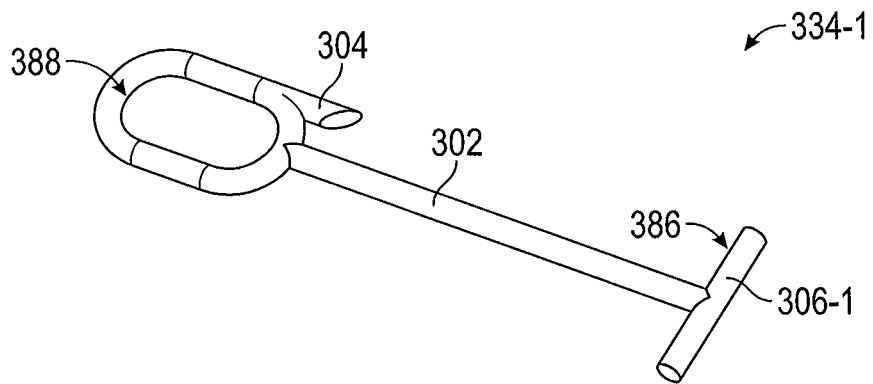
FIGS. 29-34 are perspective views of variations of another fastener having a linear filament segment and a needle guide with a single retention element configured for use with a single-needle fastening device.
Figure 32:
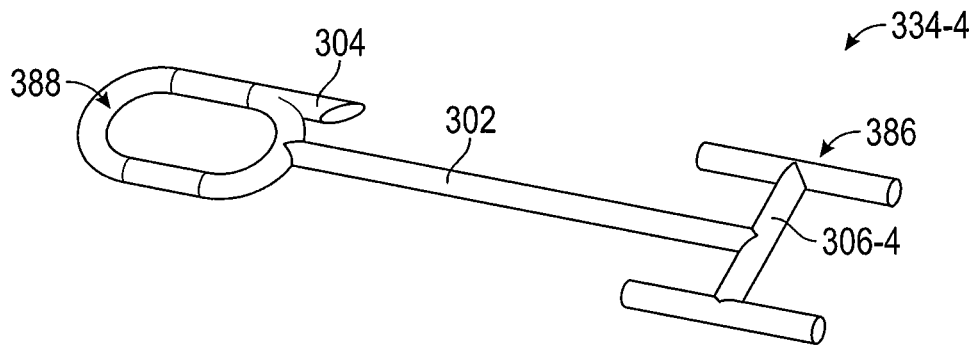
Figure 33:
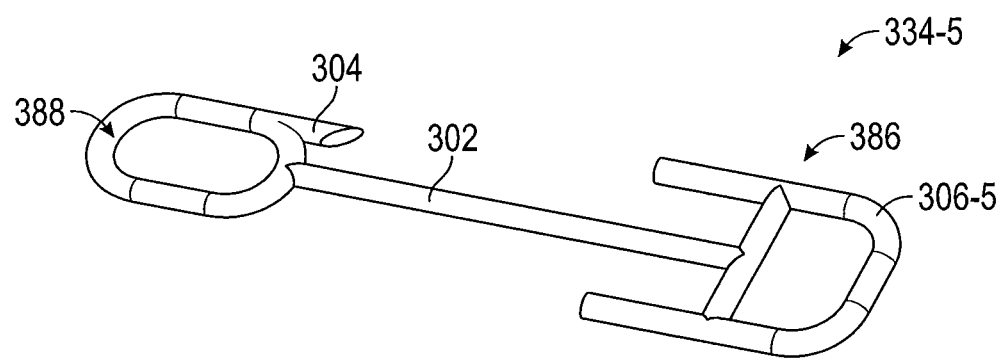
Figure 34:
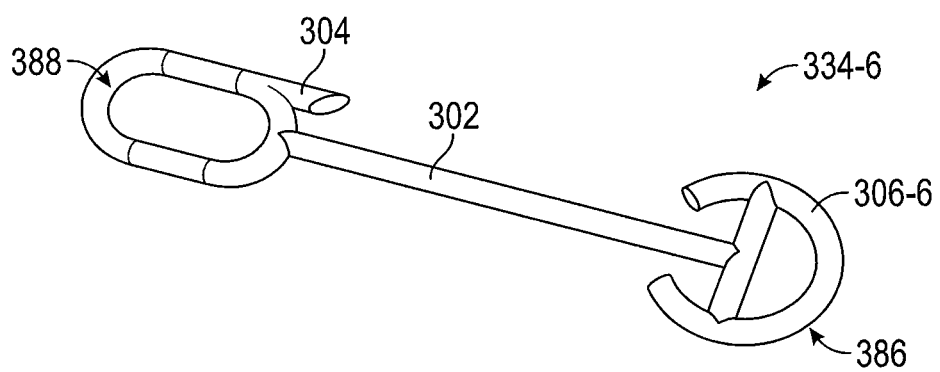
Figure 35:
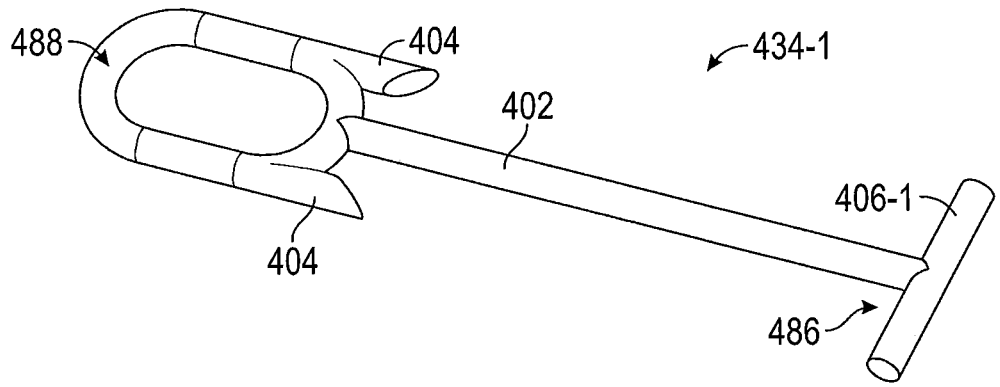
FIGS. 35-40 are perspective views of variations of another fastener having a linear filament segment and a needle guide with two retention elements configured for use with a single-needle fastening device.
Figure 38:
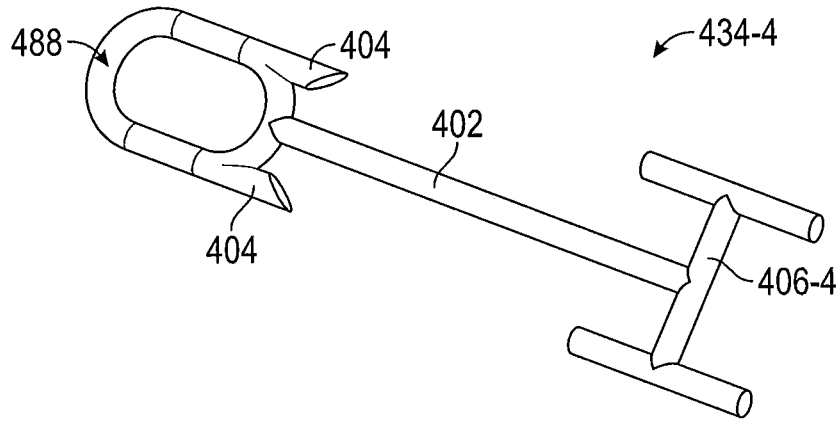
Figure 39:
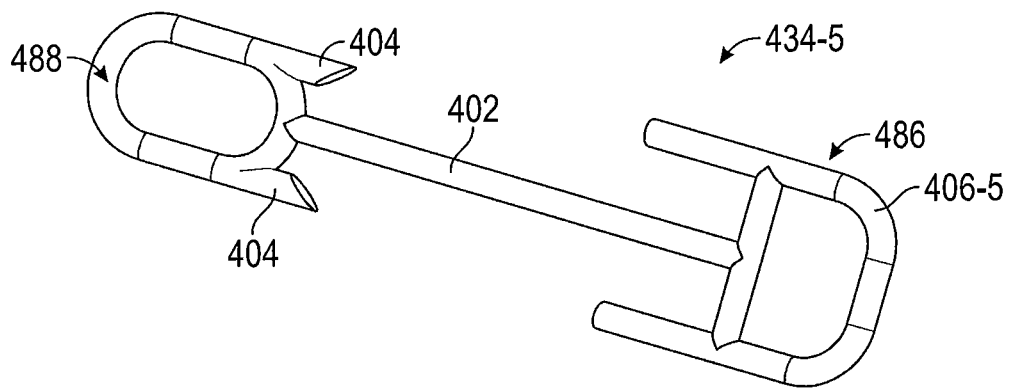
Figure 40:
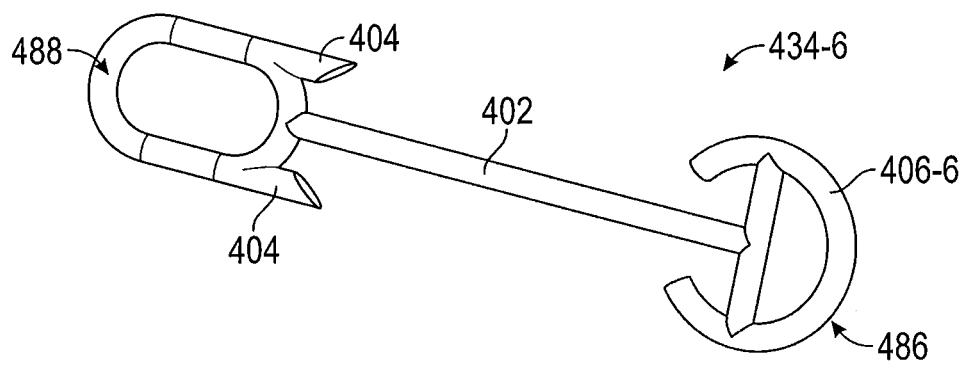

Additionally, each of the retention members 206-4, 306-4, 406-4 in FIGS. 26, 32 and 38 may provide an H-shaped configuration of prongs which generally parallel the respective filament 202, 302, 402 and lie within a plane that is coplanar to that of the fastener 234-4, 334-4, 434-4. In FIGS. 27, 33 and 39, each of the retention members 206-5, 306-5, 406-5 may provide a generally A-shaped configuration of prongs arranged to oppose advancement thereof through tissue and lying within a plane that is coplanar to that of the fastener 234-5, 334-5, 434-5. Similarly, in FIGS. 28, 34 and 40, each of the retention members 206-3, 306-3, 406-3 may provide an inwardly rounded configuration of prongs arranged to resist advancement thereof through tissue and lying within a plane that is coplanar to that of the fastener 234-6, 334-6, 434-6. While only certain embodiments of fasteners 234, 334, 434 have been provided in FIGS. 23-40, it will be understood that further alternatives or variations will be apparent to those skilled in the art without departing from the scope of the appended claims.

Figure 43:
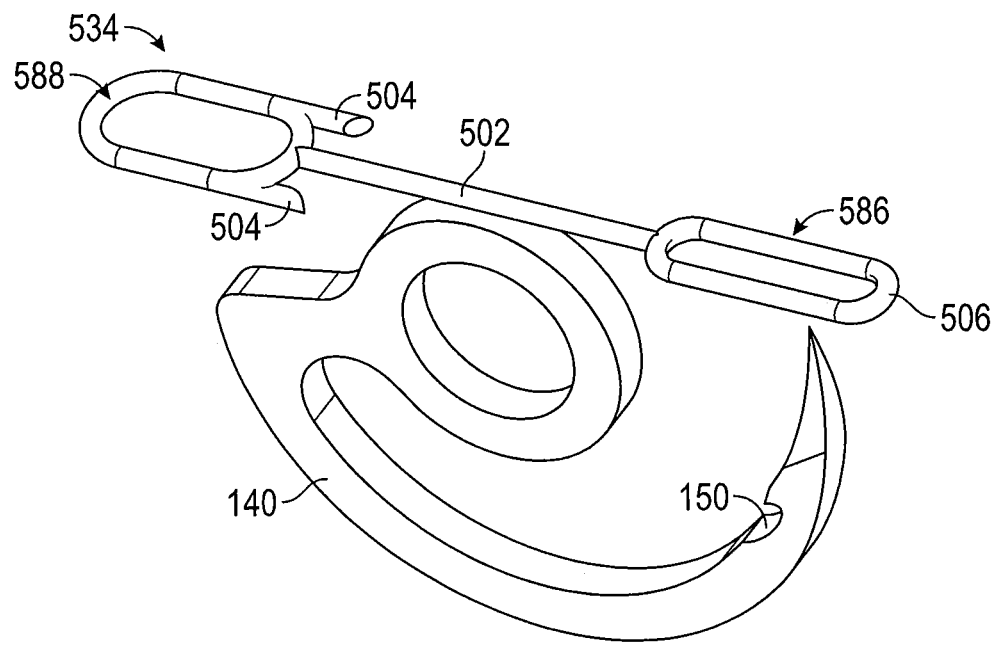
FIGS. 43-44 are perspective views of the fastener of FIG. 41 being engaged by a single arcuate needle.
Figure 44:
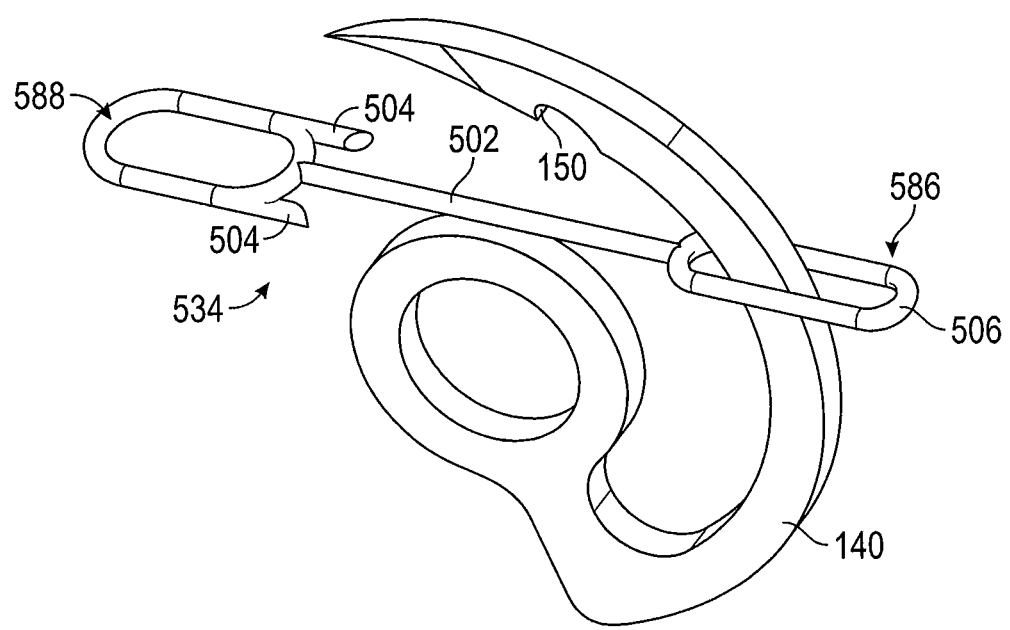
Figure 45:
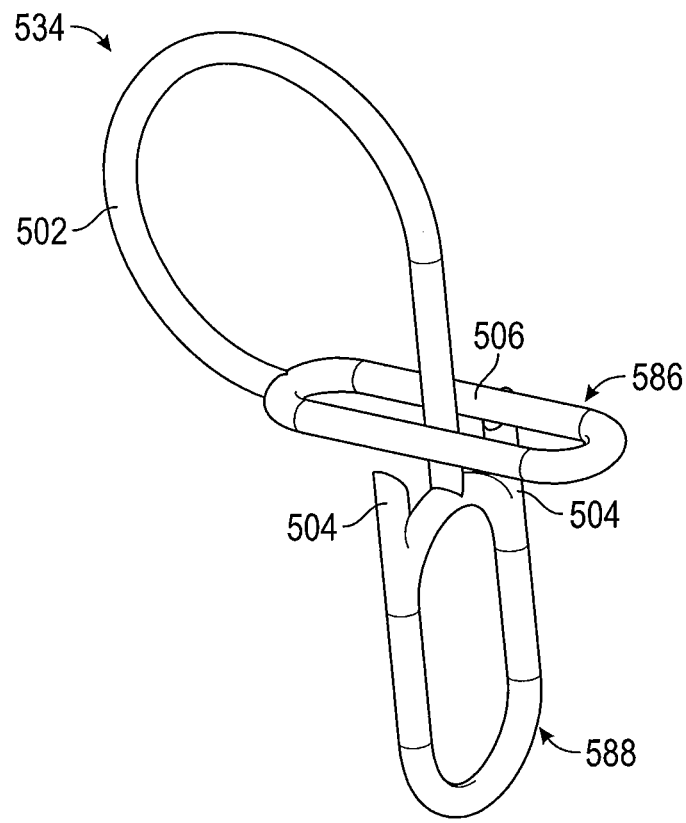
FIGS. 45-46 are perspective views of the fastener of FIG. 41 being deployed in an interlocked state.
Figure 46:
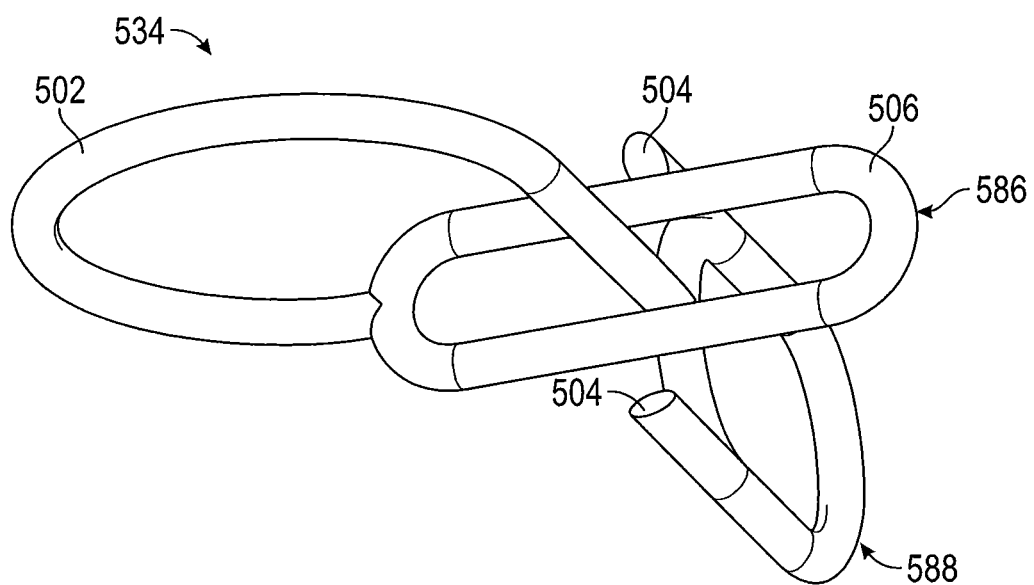
Figure 47:
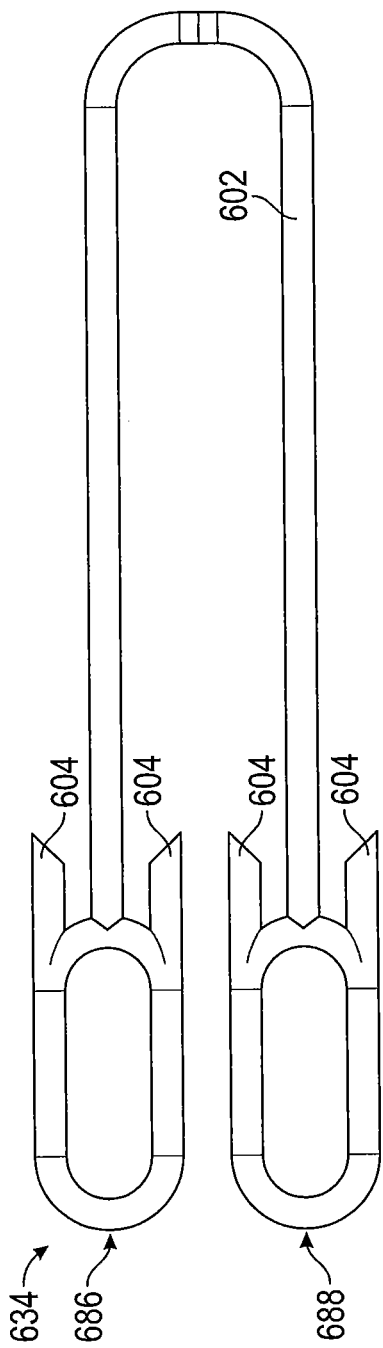
FIG. 47 is a top plan view of another fastener having two leading ends configured for use with a dual-needle fastening device.
Figure 48:
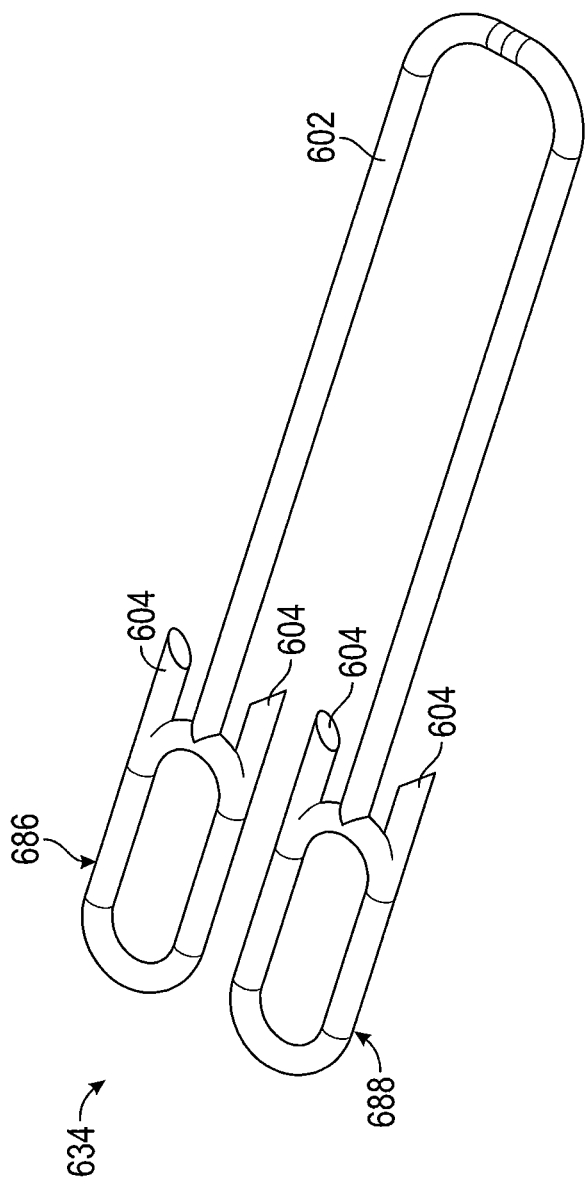
FIG. 48 is a perspective view of the fastener of FIG. 47.
Figure 49:
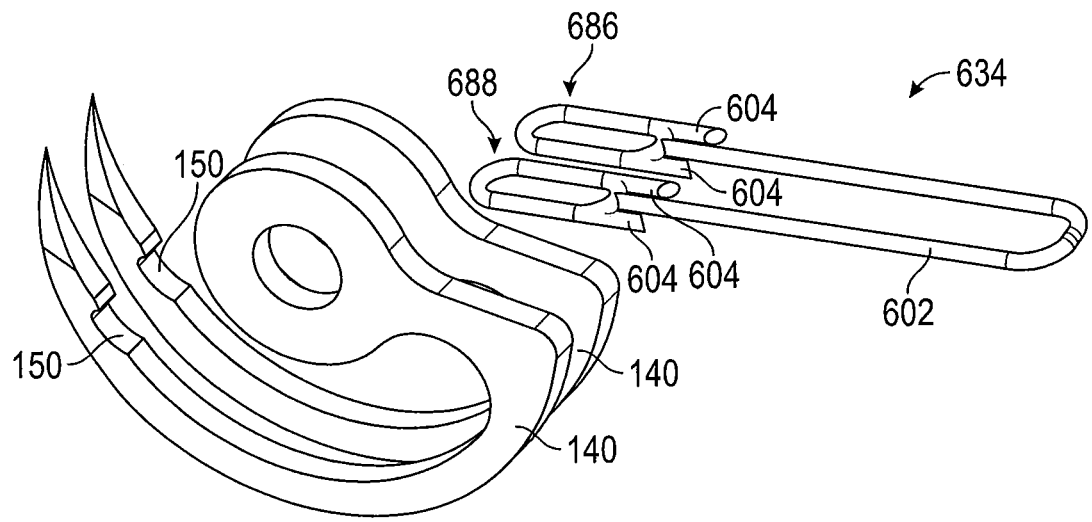
FIGS. 49-50 are perspective views of the fastener of FIG. 47 being engaged by two arcuate needles.

Turning to FIGS. 41-46, another possible embodiment of a fastener 534 that may be employed in conjunction with a single-needle configuration is provided. Similar to previous embodiments, the fastener 534 may include an elongated filament 502 linearly extending between a leading end 588 and a trailing end 586. At the leading end 588, the fastener 534 may provide a needle guide configuration having canted retention elements 504 tangentially extending therefrom in a manner which promotes advancement of the fastener 534 through tissue but resists retraction. At the trailing end 586, the fastener 534 may include a relatively open retention member 506 configured to interlock with the leading end 588 once installed. More particularly, the open trailing end 586 of a fastener 534 to be installed may be positioned directly above the advancing end of a single arcuate needle 140, as shown in FIG. 43, such that the arcuate needle 140 advances therethrough once actuated, as shown in FIG. 44. Once fully extended, the recess or hook 150 of the arcuate needle 140 may be configured to engage the leading end 588 of the fastener 534. As the arcuate needle 140 retracts, the flexible leading end 588 of the fastener 534 may be caused to be inserted fully through the open trailing end 586. As shown in FIGS. 45-46, the fastener 534 may be retained within tissue by the interlocking nature of the retention elements 504 of the leading end 588 with the open retention member 506 of the trailing end 586.

Figure 50:
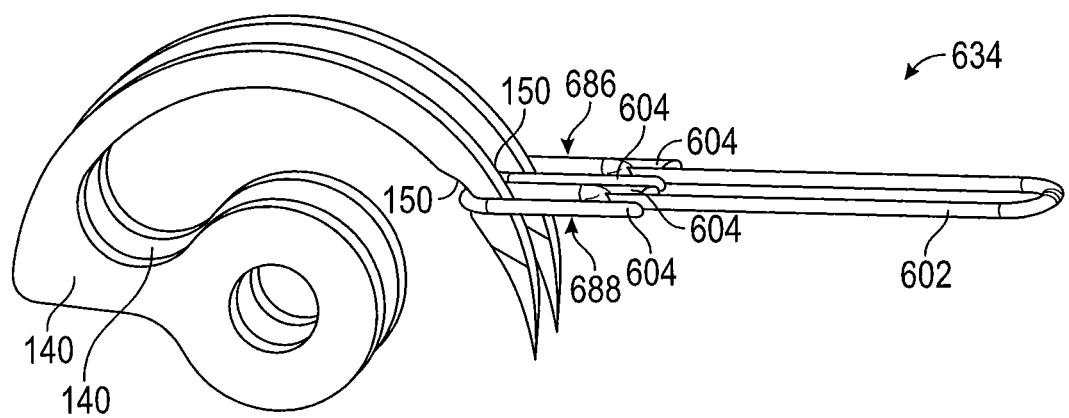

Referring now to FIGS. 47-50, yet another embodiment of a fastener 634 that may be used in conjunction with the teachings of the present disclosure is provided. As shown, the fastener 634 may include a first end 686 and a second end 688, both of which are configured in the form of leading ends. More particularly, each of the first and second ends 686, 688 may include a needle guide having one or more retention elements 604 tangentially extending therefrom in a manner configured to facilitate advancement through tissue but resist retraction. As further shown in FIGS. 49-50, the fastener 634 of FIGS. 47-48 may be installed using a fastening device employing a dual-needle configuration, or having two arcuate needles 140 coaxially disposed relative to one another. Moreover, each of the arcuate needles 140 may be operatively driven by a drive mechanism in a manner configured to, upon actuation, simultaneously advance both arcuate needles 140 in a forward rotation through tissue and engage respective ends 686, 688 of a fastener 634 to be installed, as shown in FIG. 50, and upon release, simultaneously retract both arcuate needles 140 in a reverse rotation through tissue to pull the engaged ends 686, 688 of the fastener 634.

From the foregoing, it can be seen that the present disclosure sets forth a medical fastening device adapted to rapidly and reliably install fasteners to secure tissue and/or any applicable prosthetic material. The device not only greatly reduces the time required for fastening tissues, but also results in superior ease of use relative to other methods.

Furthermore, through the unique combination of elements set forth in the present disclosure, the tissue fastening is more reliably retained with reduced irritation and other complications to the patient and without adversely affecting the integrity of the attachment and/or closure.

What is claimed is:

1. A tissue fastener, comprising:
   an elongated filament having a leading end and a trailing end;
   a needle guide disposed adjacent and connected to the leading end, the needle guide having, a shape of one of a loop, circle, ellipse, and an oval; and
   a retention member disposed adjacent and connected to the trailing end, the retention member being configured to resist advancement through at least, one of a tissue and a prosthetic material,
   wherein the retention member of the trailing end includes an open loop configured to receive the needle guide of the leading end therethrough and interlock therewith upon installation, and wherein the tissue fastener has a helical configuration upon installation.

2. The tissue fastener of claim 1, wherein the needle guide shape is configured to be engaged by a needle during deployment, the needle guide shape being configured to facilitate advancement of the needle guide through at least one of the tissue and the prosthetic material while resisting retraction thereof.

3. The tissue fastener of claim 1, wherein the needle guide of the leading end includes at least one retention element tangentially extending therefrom, the retention element being configured to resist retraction through at least one of the tissue and the prosthetic material and interlock with the retention member.

4. The tissue fastener of claim 1, wherein the leading end includes at least one retention element having one or more of a tine, a fin, and a canted element, the retention element being configured to resist retraction thereof.

5. The tissue fastener of claim 1, wherein the elongated filament includes one or more of linear and nonlinear segments.

6. The tissue fastener of claim 1, wherein the retention member includes at least one outwardly extending element that lies within a plane which at least partially intersects with a plane of the needle guide.

7. A tissue fastener, comprising:
   an elongated filament having a leading end and a trailing end;
   a needle guide disposed adjacent and connected to the leading end, the needle guide having a shape of one of a loop, circle, ellipse, or an oval and at least one retention element tangentially extending therefrom;
   a retention member disposed adjacent and connected to the trailing end, the retention member being configured to resist advancement through at least one of a tissue and a prosthetic material,
   wherein the retention member includes an open loop configured to receive the needle guide of the leading end therethrough to form a, annular configuration upon installation and interlock with the at least one retention element upon installation.

* * * * *